US005945329A

United States Patent [19]
Breddam et al.

[11] Patent Number: 5,945,329
[45] Date of Patent: Aug. 31, 1999

[54] CUSTOMIZED PROTEASES

[75] Inventors: Klaus Breddam, Glostrup; Morten C. Kielland-Brandt; Uffe Hasbo Mortensen, both of Copenhagen; Kjeld Ove Olesen; Henning Ralf Stennicke, both of Frederiksberg, all of Denmark; Fred W. Wagner, Walton, Nebr.

[73] Assignee: Carlsberg A/S, Copenhagen, Denmark

[21] Appl. No.: 08/899,324

[22] Filed: Jul. 23, 1997

Related U.S. Application Data

[63] Continuation of application No. 08/329,892, Oct. 27, 1994, which is a continuation-in-part of application No. 08/144,704, Oct. 28, 1993, abandoned.

[51] Int. Cl.⁶ ............. C12N 9/60; C12N 15/11; C12N 15/57; C12P 21/00
[52] U.S. Cl. .......... 435/223; 435/68.1; 435/69.1; 435/471; 435/476; 435/483; 435/254.21; 435/320.1; 536/23.2
[58] Field of Search ............... 435/223, 69.1, 435/252.3, 254.11, 320.1, 471, 481, 483, 68.1, 476, 254.21; 536/23.2

[56] References Cited

U.S. PATENT DOCUMENTS

| 4,339,534 | 7/1982 | Johansen et al. ............... 435/68.1 |
| 4,806,473 | 2/1989 | Johansen et al. ............... 435/68.1 |
| 4,959,312 | 9/1990 | Sirotkin ....................... 435/91.5 |
| 5,049,656 | 9/1991 | Lewis et al. .................. 530/334 |
| 5,185,258 | 2/1993 | Caldwell et al. ............... 435/220 |

FOREIGN PATENT DOCUMENTS

| 0 085 516 | 8/1983 | European Pat. Off. . |
| 63-233788 | 9/1988 | Japan . |
| WO 80/02157 | 10/1980 | WIPO . |
| 92/02615 | 2/1992 | WIPO . |

OTHER PUBLICATIONS

Olesen, et al. "The Activity of Carboxypeptidase Y toward Substrates with Basic P₁Amino Acid Residues Is Drastically Increased by Mutational Replacement of Leucine 178", *Biochemistry*, 33:11121–11126 (1994).

Watson, J.D,. et al, in The Molecular Biology of the Gene, "The genetic systems provided by *E. Coli* and its viruses (excerpt)", pp. 180–182 (1987).

Schwarz A., et al., Methods in Enzymology, vol. 184, "Enzymatic C–terminal Biotinylation of Proteins", pp. 160–166 (1990).

Carlsberg Res. Commun., vol. 50, 1985, pp. 273–284, J. Winther et al., "Increased Hydrophobicity of the S1' Binding Site in Carboxypeptidase Y Obtained by Site–Directed Mutagenesis".

BioMed., Biochim. ACTA, vol. 50, No. 10/11, 1991, pp. 157–162, J. Bongers, "Comparison of Enzymatic Semisythesis of Peptide Amides: Human Growth Hormone Releasing Factor and Analogs".

Biochemistry, vol. 33, 1994, pp. 508–517, U. Mortensen et al., "Site–Directed Mutagenesis on (Serine) Carboxypeptidase Y".

Protein Engineering, vol. 6, No. 8, 1993, pp. 927–937, R. Siezen et al., "Engineering of the Substrate–Binding Region of the Subtilisin–Like Cell–Envelope Proteinase of Lactococcus Lactis".

Alexander, et al., "Engineering the Zinc Binding Site of Human Carbonic Anhydrase II: Structure of the His–94–Cys Apoenzyme in a New Crystalline Form", *Biochemistry*, 32,,pp. 1510–1518, (1993).

Behravan, et al. "Fine tuning of the catalytic properties of human carbonic anhydrase II", *Eur. J. Biochem.*, 195, pp. 393–396, (1991).

Behravan, et al., "Structural and functional differen3ces between carbonic anhydrase isoenzymes I and II as studied by site–directed mutagenesis", *Eur. J. Biochem.*, 198, pp. 589–592, (1991).

Bracey, et al., "Spinach Carbonic Anhydrase: Investigation of the Zinc–Binding Ligands by Site–Directed Mutagenesis, Elemental Analysis, and EXAFS", *Biochemistry*, 33, pp. 13126–13131, (1994).

Chen, et al., "Interaction and influence of Phenylalanine–198 and Threonine–199 on Catalysis by Human Carbonic Anhydrase III", *Biochemistry*, 32, pp. 7861–7865, (1993).

Fierke, et al., "Functional Consequences of Engineering the Hydrophobic Pocket of Carbonic Anhydrase II", *Biochemistry*, 30, pp. 11054–11063, (1991).

(List continued on next page.)

Primary Examiner—Charles L. Patterson, Jr.
Assistant Examiner—William W. Moore
Attorney, Agent, or Firm—Merchant, Gould, Smith, Edell, Welter & Schmidt, P.A.

[57] ABSTRACT

The invention provides customized proteases (i.e., mutant enzymes), methods of making customized proteases, as well as methods of using customized proteases. The customized proteases of the invention are derived from the known proteases. Altered transacylation reactions include the capability to perform transacylation reactions not substantially catalyzed by the known protease or the capability to perform transacylation reactions with improved yields, or both. The methods of the invention provide for customized proteases through site specific or random mutagenesis of the active site amino acids of the known proteases. The invention also provides for methods of using the customized proteases to prepare a preselected transacylation products. The preselected transacylation products produced can be modified by substitution at the N- or C-terminal with nucleophiles such as L-amino acids, D-amino acids, amino acid amides, and radioactive amino acids.

32 Claims, No Drawings

OTHER PUBLICATIONS

Jewell, et al., "Enhancement of the Catalytic Properties of Human Carbonic Anhydrase III by Site–Directed Mutagenesis", *Biochemistry*, 30, pp. 1484–1490, (1991).

Kiefer, et al., "Engineering a Cysteine Ligand into the Zinc Binding Site of Human Carbonic Anhydrase II", *Biochemistry*, 32, pp. 9896–9900, (1993).

Krebs et al., "Determinants of Catalytic Activity and Stability of Carbonic Anhydrase II as Revealed by Random Mutagenesis", *J. Bio. Chem.*, 268, pp. 948–952 (1993).

Krebs, et al., "Structural and Functional Importance of a Conserved Hydrogen Bond Network in Human Carbonic Anhydrase II", *J. Bio. Chem.*, 268, pp. 27458–27466, (1993).

Krebs, et al., "Kinetic and Spectroscopic Studies of Hydrophilic Amino Acid Substitutions in the Hydrophobic Pocket of Human Carbonic Anhydrase II", *Biochemistry*, 32, pp. 4496–4505, (1993).

LoGrasso, et al., "Influence of Amino acid Replacement at Position 198 on Catalytic Properties of Zinc–Bound Water in Human Carbonic Anhydrase III", *Biochemistry*, 32, pp. 5786–5791, (1993).

Martensson, et al., "Characterization of Folding Intermediates of Human Carbonic Anhydrase II: Probing Substructure by Chemical Labeling of SH Groups Introduced by Site–Directed Mutagenesis", *Biochemistry*, 32, pp. 224–231, (1993).

Ren, et al., "Same properties of site–specific mutants of human carbonic anhydrase II having active–site residues characterizing carbonic anhydrase III", *J. Biochem.*, 201, pp. 417–420, (1991).

Taoka, et al., "Comparison of Intra–and Intermolecular Proton Transfer in Human Carbonic Anhydrase II", *J. Bio. Chem.*, 269, pp. 17988–17992, (1994).

Taoka, et al., "Catalysis by mutants of human carbonic anhydrase II: effects of replacing hydrophobic resides 198 and 204", *Biochimia et Biophysica Acta*, 1159, pp. 274–278, (1992).

Tu, et al., "Interactions of Active–site Residues and Catalytic Activity of Human Carbonic Anhydrase III", *J. Bio. Chem.*, 37, pp. 23002–23006, (1994).

Tu, et al., "Kinetic Analysis of a Mutant (His–Tyr) Responsible for Human Carbonic Anhydrase II Deficiency Syndrome", *J. Bio. Chem.*, 268, pp. 4775–4779, (1993).

Tweedy, et al., "Structure and Energetics of a Non–Proline cis–Peptidyl Linkage in a Proline–202–Alanine Carbonic Anhydrase II Variant", *Biochemistry*, 32, pp. 10944–10949, (1993).

Endrizzi et al., *Biochemistry* 33:11106 (1994).

Blachyl–Dyson et al., "Yeast Carboxypeptidase Y Can Be Translocated and Glycosylated Without its Amino–terminal Signal Sequence", *J. Cell Biol.*, 104:1183–1191 (1987).

Bongers et al., "Semisynthesis of Human Growth Hormone–Releasing Factor by Trypsin Catalyzed Coupling of Leucine Amide to a C–Terminal Acid Precursor" *Int. J. Peptide Protein Res.*, 40:268–273 (1992).

Botstein et al., "Sterile Host Yeasts (SHY): A Eukaryotic System of Biological Containment for Recombinant DNA Experiments", *Gene*, 8:17–24 (1979).

Breddam et al., "Semisynthesis of Human Insulin Utilizing Chemically Modified Carboxypeptidase Y", *Carlsberg Res. Comm.*, 49:463–472 (1984).

Breddam et al., "Chemically Modified Carboxypeptidase Y with Increased Amidase Activity", *Carlsberg Res. Comm.*, 49:535–554 (1984).

Breddam et al., "Determination of C–Terminal Sequences by Digestion with Serine Carboxypeptidases: The Influence of Enzyme Specificity", *Carlsberg Res. Commun.*, 52:55–63 (1987).

Breddam et al., "Amidation of Growth Hormone Releasing Factor (1–29) by Serine Carboxypeptidase Catalyzed Transpeptidation", *Int. J. Peptide Res.*, 37:153–160 (1991).

Busby et al., "Isolation of Mutant Promoters in the *Escherichia coli* Galactose Operon Using Local Mutagenesis on Cloned DNA Fragments", *J. Mol. Biol.*, 154:197–209 (1982).

F. Dal Degan et al., "Purification and Characterization of Two Serine Carboxypeptidase from *Aspergillus niger* and Their Use in C–terminal Sequencing of Proteins and Peptide Synthesis", *Appl. Environ. Microbiol.*, 58:2144–2152 (1992).

Dierks et al., "Three Regions Upstream from the Cap Site Are Required for Efficient and Accurate Transcription of the Rabbit beta–Globin Gene in Mouse 3T6 Cells", *Cell*, 22:659–706 (1983).

Dodson et al., "Mutagenesis of Bacteriophage T7 in vitro by incorporation of $O^6$–methylguanine During DNA Synthesis", *PNAS*, 79:7440–7444 (1982).

Dower et al., "High Efficiency Transformation of *E. coli* by High Voltage Electroporation", *Nucleic Acid Res.*, 16:6127 (1988).

Eadie et al., "Mechanism of Mutagenesis by $O^6$–methylguanine", *Nature* 308:201–203 (1984).

Flavell et al., "Site–Directed Mutagenesis: Generation of an Extracistronic Mutation in Bacteriophage Qbeta RNA", *J. Mol. Biol.*, 89:255–272 (1974).

Grossberger et al., "Incorporation into DNA of the Base Analog 2–aminopurine by the Epstein–Barr Virus–Induced DNA Polymerase in vivo and in vitro", *PNAS*, 78:5689–587 (1981).

Hayashi, "Carboxypeptidase Y", *Methods Enzymol.*, 45:568–587 (1976).

Henriksen et al., "Peptide Amidation by Chemical Protein Engineering: A Combination of Enzymatic and Photochemical Synthesis", *J. Am. Chem. Soc.*, 114:1876–1877 (1992).

Ito et al., "Transformation of Intact Yeast Cells Treated with Alkali Cations", *J. Bacteriol.*, 153:163–168 (1983).

Kadonga et al., "A Simple and Efficient Method for Chemical Mutagenesis of DNA", *Nucl. Acids. Res.*, 13:1733–1745 (1985).

Kramer et al., "Different Base/Base Mismatches are Corrected with Different Efficiencies by the Methyl–Directed DNA Mismatch–Repair System of *E. Coli*", *Cell*, 38:879 (1984).

Kunkel et al., "On the Fidelity of DNA Replication: Effect of Divalent Metal Ion Activators and Deoxyribonucleoside Triphosphate Pools on in vitro Mutagenesis", *J. Biol. Chem.*, 254:5718–5725 (1979).

Lewis et al., "Efficient Site Directed in vitro Mutagenesis Using Ampicillin Selection", *Nucleic Acids Res.*, 18:3439 (1990).

Liao et al., "Structure of Wheat Serine Carboxypeptidase II at 3.5–A Resolution", *J. Biol. Chem.*, 265:6528–6531 (1990).

Loeb, "Apurinic Sites as Mutagenic Intermediates", *Cell*, 40:483–484 (1985).

Mott et al., "Targeted Mutagenesis in vitro: lac Repressor Mutations Generated Using AMV Reverse Transcriptase and dBrUTP", *Nucl. Acids Res.,* 12:4139–4152 (1984).

Myers et al., "A General Method for Saturation Mutagenesis of Cloned DNA Fragments", *Science,* 229:242–247 (1985).

Nielsen et al., "Regulated Overproduction and Secretion of Yeast Carboxypeptidase Y", *Appl. Microbiol. Biotech.,* 33:307–312 (1990).

Ohsuye et al., "Cloning of cDNA Encoding a New Peptide C–terminal alpha–Amidating Enzyme Having a Putative Membrane–Spanning Domain from Xejopus Laevis Skin", *Biochem. Biophys. Res. Commun.,* 150:1275–1281 (1988).

Olesen et al., "Altering Substrate Preference of Carboxypeptidase Y by a Novel Strategy of Mutagenesis Eliminating Wild Type Background", *Protein Engineering,* 6:409–415 (1993).

Robinson et al., "Protein Sorting in *Saccharomyces cerevisiae:* Isolation of Mutants Defective in the Delivery and Processing of Multiple Vacuolar Hydrolases", *Mol. Cell. Biol.,* 8:4936 (1988).

Rothman et al., "Protein Sorting in Yeast: Mutants Defective in Vacuole Biogenesis Mislocalize Vacuolar Proteins into the Late Secretory Pathway", *Cell,* 47:1041–1051 (1986).

Sakina et al., "Thermolysin–Catalyzed Synthesis of Peptide Amides", *Chem. Pharm. Bull.,* 36:4345–4354 (1988).

Sakina et al., "Protease–Catalyzed Semisynthesis of Human Neuropeptide Y", *Chem. Phar. Bull.,* 37:811–812 (1989).

Schiestl et al., "High Efficiency Transformation of Intact Yeast Cells Using Single Stranded Nucleic Acids as a Carrier", *Curr. Genet.,* 16:339 (1992).

Sherman, "Getting Started with Yeast", *Methods Enzymol.,* 194:3–21 (1991).

Shortle et al., "Directed Mutagenesis with Sodium Bisulite", *Methods Enzymol.,* 100:457–468 (1983).

Sorensen et al., "Primary Structure of Carboxypeptidase II from Malted Barley", *Carlsberg Res. Commun.,* 52:285 (1987).

Stevens et al., "Gene Dosage–dependent Secretion of Yeast Vacuolar Carboxypeptidase Y", *J. Cell Biol.,* 102:1551–1557 (1986).

Stevens et al., "Translocation, Sorting and Transport of Yeast Vacuolar Glycoproteins", *Yeast Cell Biology,* Editor: J. Hicks, New York, Alan R. Liss, at pp. 519–536 (1986).

Tullin et al., "A High–Affinity Uptake System for Branched––Chain Amino Acids in *Saccharomyces cerevisiae*", *Yeast,* 7:933–941 (1991).

Valls et al., "Protein Sorting in Yeast: The Localization Determinant of Yeast Vacuolar Carboxypeptidase Y Resides in the Propeptide", *Cell,* 48:887–889 (1987).

Winther et al., "Yeast Carboxypeptidase Y Requires Glycosylation for Efficient Intracellular Transport, But Not for Vacuolar Sorting, in vivo Stability, or Activity", *Eur. J. Biochem.,* 179:681 (1991).

Wylie et al., "Monoclonal Antibodies Specific for Mercuric Ions", *Proc. Natl. Acad. USA,* 89:4104–4108 (1992).

Yanisch–Perron et al., "Improved M13 Phage Cloning Vectors and Host Strains: Nucleotide Sequences of the M13mp18 and pUC19 Vectors", *Gene,* 33:103 (1985).

Zell et al., "DNA Mismatch–Repair in *Escherichia coli* Counteracting the Hydrolytic Deamination of 5–methyl–cytosine Residues", *EMBO J.,* 6:1809 (1987).

Bech et al., "Chemical Modifications of a Cysteinyl Residue Introduced in the Binding Site of Carboxypeptidase Y By Site–Directed Mutagenesis", *Carlsberg Res. Commun.,* 53:381 (1988).

CUSTOMIZED PROTEASES

CROSS REFERENCE TO RELATED APPLICATION

This is a Continuation of application Ser. No. 08/329,892, filed Oct. 27, 1994, which application is a continuation-in-part of U.S. patent application Ser. No. 08/144,704, filed Oct. 28, 1993, and now abandoned.

BACKGROUND OF THE INVENTION

Peptides used for pharmaceutical purposes will, in the future, more frequently be produced through the exploitation of genetic engineering. However, genetic engineering has limits to its capabilities. For example, expression of recombinant peptides bearing non-naturally occurring L-amino acids, D-amino acids, radioactive amino acids, and other detectable labels is not possible through recombinant techniques because there is no genetic code which codes for these modifications. In addition, naturally occurring amino acid modifications such as C-terminal amide group substitution, which are routinely performed in vivo, are difficult to perform in vitro. These post-translation modifications are important because they often result in the most potent or longest acting form of the peptide and constitute the naturally occurring form of the peptide often needed for pharmaceutical use.

There are techniques for modification of recombinant peptides. One such technique is C-terminal α-carboxyl amidation, as described by Bongers et al., *Int. J. Peptide Protein Res.*, 40:268 (1992) utilizing an α amidating enzyme as described in Henriksen et al., *J. Am. Chem. Soc.*, 114:1876–1877 (1992); and Ohsuye et al., *Biochem. Biophys. Res. Commun.*, 150:1275–1281 (1988). However, these techniques are limited to those modifications for which there exists a natural enzyme or chemical method capable of performing the desired modification.

Amidation of peptides has been performed through protease catalyzed replacement reactions (transpeptidation) using an amino acid amide or peptide amide as a nucleophile. Sahina et al., *Chem. Pharm. Bull.*, 36:4345–4354 (1988); Sahina et al., *Chem. Pharm. Bull.*, 37:811–812 (1989); Breddam et al., *J. Peptide Protein Res.*, 37:153–160 (1991). Yields using these techniques are typically quite low. However, transpeptidation reactions catalyzed by serine or thiol-proteases, under appropriate reaction conditions, have been carried out in high yields. Breddam et al. (1991) cited supra. Although protease catalyzed transpeptidation can be very effective under some circumstances, it is limited to substrates for which a natural protease exists and which exhibits specificity for a peptide bond close to the C-terminus.

Hence, there is a need to provide mutant protease enzymes capable of performing heretofor unknown N- or C-terminal modifications as well as peptide chain elongation with a variety of substrates, especially those substrates that are not reactive with the naturally occurring protease enzyme.

SUMMARY OF THE INVENTION

These and other objectives are provided for by the method of the invention. The invention provides customized proteases (i.e., mutant proteases), methods of making customized proteases, as well as methods of using customized proteases.

Customized proteases are derived from known proteases such as endoproteases, exoproteases, serine proteases and cysteine proteases. A customized protease is a modified version of a known protease designed to provide a protease that is capable of transacylating a preselected substrate with a preselected nucleophile in a transacylation reaction not substantially catalyzed by the known protease. The mutant or customized protease can also exhibit improved or enhanced yields of transacylation. The preferred preselected substrates are peptides having an acidic or basic amino acid at the penultimate position. The preferred preselected nucleophiles are amino acids and amino acid derivatives such as amino acid esters and amino acid amides.

The invention also provides methods for preparing a customized protease. These methods can involve site specific mutagenesis or random mutagenesis. Site specific mutagenesis can involve replacing a selected amino acid in the active site with a selected amino acid or by replacing the selected active site amino acid with any one of the 20 amino acids randomly. Random mutagenesis can involve replacing any amino acid of the active site with any of the other 19 amino acids.

One method of the invention involves providing a DNA sequence that encodes the known protease, modifying at least one codon for at least one amino acid in the active site to form a mutant DNA sequence, and transforming a suitable host cell with the mutant DNA to provide for expression of the customized protease. In a preferred version, the codon for the amino acid in the active site is deleted using restriction enzymes and the deleted codon is replaced with an oligonucleotide encoding a different amino acid residue.

Another method of the invention involves modifying a DNA sequence encoding the known protease by inserting stop codons and/or a restriction enzyme recognition site at targeted sites to form a modified DNA sequence encoding an inactive protease. The targeted site preferably includes a codon for an amino acid in the active site which is replaced by the stop codon. A mutant DNA strand is synthesized and amplified by incubating the modified DNA strand in the presence of synthetic enzymes and oligonucleotides and a first degenerate oligonucleotide. The first degenerate oligonucleotide contains a codon for a different amino acid in the targeted site and in place of the amino acid in the active site in the known protease. The mutant DNA strand is then selected and screened by detecting the presence of the customized protease.

The invention also includes a method of using customized proteases to modify a preselected substrate by transacylation. The transacylation reaction catalyzed by the customized protease is preferably not substantially transacylated by the known enzyme. A customized protease ins incubated with a preselected substrate and a preselected nucleophile to form a mixture. The mixture is incubated sufficiently to form a preselected transacylation product, preferably in high yield.

Customized proteases according to the invention can be utilized for post translation modification of recombinant peptides. The transacylation products produced are modified by substitution at the C-terminal or N-terminal end with various nucleophiles (including L-amino acids, D-amino acids, amino acid amides, amino acid derivatives, amino acid esters and radioactive amino acids or peptide derivatives including two or more amino acids of which the terminal amino acid is a natural amino acid or an amino acid derivative). It is understood that peptides produced by means other than recombinant technology can be transacylated according to the method of the invention.

DETAILED DESCRIPTION OF THE INVENTION

The invention provides customized proteases (i.e., mutant enzymes), methods of making the customized proteases, as well as methods of using the customized proteases.

The customized proteases of the invention are derived from known proteases and have transacylation capabilities differing from the known proteases. Altered transacylation capabilities include the capability to perform transacylation reactions not substantially catalyzed by the known protease (i.e. yields less than 10%) or the capability to perform transacylation reaction with improved or enhanced yields (i.e., 80 to 100%) or both. The mutant customized proteases have been modified so that the protease can perform transacylation reactions with different preselected substrates and/ or different preselected nucleophiles than the known protease. The mutant enzymes can also be specifically designed and selected to perform transacylation reactions with a specific preselected substrate and/or nucleophile. A known protease, preferably an exopeptidase, can be customized by replacement of amino acids in the active site so that the customized enzyme can transacylate different preselected substrates and/or nucleophiles. The customized protease can also exhibit enhanced or improved yields of transacylation. Preselected substrates are preferably those that have an acidic or basic penultimate amino acid. Preselected nucleophiles are preferably acidic or basic amino acid amides.

The present disclosure will utilize the following terminology. This terminology is applicable to proteases including both carboxy- and amino peptidases, as well as endopeptidases. Schechter et al., (1967).

The amino acids of the preselected substrates are designated by the letter "P". The amino acids of the substrate on the N-terminal side of the peptide bond to be cleaved by a protease enzyme are designated $P_n \ldots P_3, P_2, P_1$, with $P_n$ being the amino acid furthest from the catalytic apparatus of the protease. Amino acids of the preselected substrate on the carboxy side of the bond to be cleaved by the protease are designated $P_1', P_2', P_3' \ldots P_n'$ with $P_n'$ being the amino acid furthest from the catalytic apparatus of the protease. The bond which is to be cleaved by the protease is the $P_1-P_1'$ bond. Hence, the generic formula for the amino acids of the preselected substrate are as follows:

carboxypeptidase $P_n \ldots P_3\text{-}P_2\text{-}P_1\text{-}P_1'$
amino peptidase $P_1\text{-}P_1'\text{-}P_2'\text{-}P_3' \ldots P_n'$
endopeptidase $P_n \ldots P_3\text{-}P_2\text{-}P_1\text{-}P_1'\text{-}P_2'\text{-}P_3' \ldots P_n'$ The "active site" of the protease is divided into a number of substrate binding sites and a catalytic apparatus. For example, the catalytic apparatus of serine proteases such as carboxypeptidase Y has a conserved catalytic triad of amino acids including serine, histidine and aspartic acid. The binding sites of the enzymes can include the $S_1$ binding site, the $S_1'$ binding site which includes the C binding site. For carboxypeptidases, the $S_1$ binding site binds the side chain of the penultimate amino acid of the preselected substrate ($P_1$), the $S_1'$ binding site binds to the side chain of the carboxy terminal amino acid ($P_1'$), and the C binding site binds the terminal α-carboxylate group. Modification of the active site preferably includes changes to amino acids in one or more of the binding sites.

The terminology for the substrate binding site of a protease is analogous to that for describing the amino acids of the preselected substrate except that the substrate binding sites of the protease are designated by the letter "S". The substrate binding sites for the amino acids on the N-terminal side of the cleaved bond are labelled as $S_n \ldots S_3, S_2, S_1$. The substrate binding sites for amino acids on the carboxy side of the cleaved bond are designated by "S'". These are labelled as $S_1'S_2' \ldots S_n'$. Also, analogous to terminology of the amino acids on the substrate, the catalytic apparatus of the protease is understood to exist between the $S_1$ and $S_1'$ substrate binding sites. Hence, a generic formula for describing substrate binding sites of a protease is:

$$S_n \ldots S_2\text{-}S_1\text{-}S_1'\text{-}S_2' \ldots S_n'.$$

The customized proteases of the invention are capable of transacylating substrates. As used herein, transacylation means that the enzyme can catalyze a reaction in which a leaving group is exchanged for a nucleophile. Transacylation reactions include transpeptidation reactions as well as peptide elongation reaction. Transpeptidation as used herein, occurs when single or multiple amino acids or amino acid derivatives act as a leaving group and the nucleophile is a single amino acid or peptide or amino acid derivative. Peptide elongation as used herein involves replacement of a single amino acid with a peptide. Transacylation reactions also include peptide elongation if the leaving group is an alcohol and the nucleophile is a single or multiple amino acid unit.

Customized proteases according to the invention can be utilized for post translation modification of recombinant peptides. The transacylation products produced are modified by substitution at the C-terminal or N-terminal end with various nucleophiles (including L-amino acids, D-amino acids, amino acid amides, amino acid derivatives, amino acid esters and radioactive amino acids or peptide derivatives including two or more amino acids of which the terminal amino acid is a natural amino acid or an amino acid derivative). It is understood that peptides produced by means other than recombinant technology can be transacylated according to the method of the invention.

The method of the invention provides for production of customized proteases through the process of site specific and/or random site mutagenesis. The invention further provides for selection and screening of suitably modified customized protease that is capable of catalyzing the preselected transacylation reaction. Alternatively, the method of the invention provides a means of producing customized protease through the process of traditional mutagenesis. The invention also provides a process for utilizing the customized protease to transacylate a preselected substrate to form modified peptide products.

A. Customized Protease

The invention provides for customized proteases. The customized proteases are derived from known proteases and have altered transacylating capabilities differing from the known proteases. As used herein, a customized protease is a modified version of a known protease designed to provide a protease that is capable of transacylating a preselected substrate with a preselected nucleophile in a transacylation reaction not substantially catalyzed by the known protease (i.e., less than 10%). The mutant or customized protease can also exhibit improved or enhanced yields of transacylation. Improved or enhanced yields are yields preferably increased to about 40 to 80%, preferably about 80 to 100% over the yields of the known enzyme. Known proteases preferably include serine proteases, cysteine proteases and other endo- and exopeptidases. The especially preferred proteases are serine carboxypeptidases. Protease enzymes are capable of hydrolyzing preselected substrates as well as transacylating substrates in which the scissile bond is an ester and/or peptide bond.

The general reaction for transacylation is shown below:

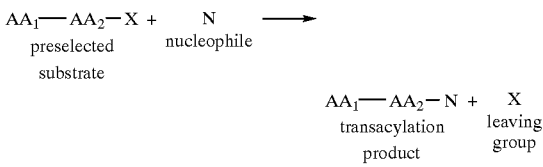

Transacylation can occur at the N or C-terminal end of the preselected substrate. While not meant to be a limitation of the invention, it is believed that an enzyme that catalyzes transacylation preferably can bind to or otherwise accommodate the nucleophile. The desired product of the reaction is designated the transacylation product.

The general reaction for hydrolysis is:

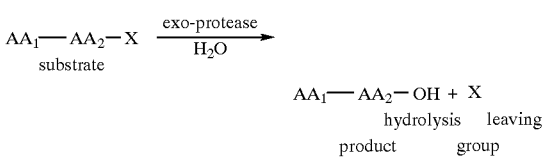

Yields of a desired transacylation product can depend on the (1) leaving group of the substrate, (2) the nucleophile, and (3) the rates of competing side reactions for the particular substrate and nucleophile. The competing side reactions can include (1) hydrolysis of the substrate, (2) hydrolysis of the desired transacylation product, (3) formation of various undesirable side products through transacylation, e.g., addition of nucleophiles to peptides originating from hydrolysis of the substrate, addition of nucleophiles to the desired transacylation product, polymerization of transacylation products, etc. Undesirable side products can include the hydrolysis product of the substrate, the hydrolysis product of the desired transacylation product, and transacylation product of the substrate with one or more of the hydrolysis products. The preferred customized protease of the invention can catalyze the desired transacylation reaction in high yields (i.e., preferably about 40 to 100% and more preferably 80 to 100%), does not form substantial amounts of undesirable side products, and has a high affinity for the nucleophile. The preferred customized protease also does not substantially form undesirable transacylation side products, especially the transacylation product of a reaction of the hydrolysis product of the substrate with the substrate. As used herein, "substantially" means that the undesirable side products preferably are about 0 to 40% of the yield and more preferably 0 to 20% of the yield and most preferably 0 to 5% of the yield. Some of the undesirable side products can be removed from the reaction mixture by modifying the side product with an antigenic capping agent and removing the capped products with an affinity column. Side products can be modified with antigenic capping agents in a manner similar to that described in U.S. Pat. No. 5,049,656 issued Sep. 17, 1991, wherein a method for modifying undesirable side products in automated peptide synthesis is described.

A preselected substrate is preferably not substantially transacylated by the known protease. The term substantially as used herein, means the yield of the transacylation reaction with the known protease is preferably about 0 to 40% and more preferably about 0 to 10%. The preselected substrate can be a naturally occurring peptide, a recombinant peptide, a synthetic peptide or a peptide in which the C-terminal α-carboxyl group has been esterified or otherwise modified. The preselected substrate has a core peptide connected to a leaving group at a terminus of the core peptide. The portion of the preselected substrate from which the leaving group is removed and to which the nucleophile is added is the core. Suitable leaving groups are amino acids, small peptides, or alcohols. The preferred leaving groups are small apolar or hydrophillic amino acids as well as moieties linked to the peptide core by an ester bond.

The suitability of the preselected substrate is dependent on the substrate specificity of the protease as well as on the nature of the leaving group and the desired final products. While not meant to be a limitation of the invention, it is believed that the suitability of the leaving group is dependent on (1) the desired modification of the preselected substrate; (2) the substrate specificity of the customized protease; and (3) the manner in which the leaving group binds to the customized protease.

A suitable preselected substrate for transacylation using a customized protease, according to the method of the invention, is of the general formula:

P—A

Wherein P represents the N-terminal or C-terminal core of the preselected substrate and A is the leaving group. The leaving group (A) can be an amino acid, an amino acid amide, a peptide, a peptide amide, or an alcohol. If A is an amino acid, amino acid amide, peptide or peptide amide, cleavage of A, from the core (P) is at the peptide bond. If A is an alcohol, cleavage of A from the core is at the ester bond. Preferably, the preselected substrate is not a substrate that is transacylated by the known protease with high efficiency (i.e., yields of about 0 to 40%). More preferably, the preselected substrate has an acidic or basic penultimate amino acid. Suitable preselected substrates include growth hormone releasing factor (GRF) and derivatives thereof, calcitonin and derivatives thereof, and glucagon-like peptide-1 (GLP-1) (SEQ ID NO:1). Preferred preselected substrates are GRF (1–43)-Ala (SEQ ID NO:2), GRF (1–24) (SEQ ID NO:3), and GLP-1 (SEQ ID NO:1).

A nucleophile, as used herein, is a molecule that donates a pair of electrons to an atomic nucleus to form a covalent bond. A suitable nucleophile can be an amino acid derivative, peptide derivative, ammonia or labelled compound which can be added to the core of the preselected substrate by the customized protease capable of substituting the leaving group for the nucleophile. A suitable nucleophile can also include agents that can be converted to achieve the desired modification of the transacylation product. For example, photonucleophiles such as those described by Buckardt can be added to the substrate by transacylation with a customized protease and the resulting transacylation product can subsequently be converted to an amide by application of light. A suitable nucleophile can be preselected based upon (1) the desired modification of the final product; and (2) the ability of the nucleophile to displace the leaving group on the preselected substrate. The preferred nucleophiles include amino acids and amino acid derivatives such as amino acid esters and amino acid amides.

Customized proteases are rendered suitable for a chosen transacylation reaction through modification of the known protease at the "active site." Modifications of the mutant or customized enzyme can be site specific mutations designed to alter the "active site" of the protease so that it can act upon different preselected substrates and/or nucleophiles than the known protease. Modifications can include substitution, deletion, or insertion of one or more amino acids. The modifications can also be generated by random mutagenesis.

Some of the amino acids in the active sites of proteases are known to those of skill in the art. When the amino acids in the active site of a protease are not known, amino acids equivalent to amino acids in known binding sites of proteases can be identified using standard methods. These methods include identification of equivalent amino acids by reference to the primary and/or tertiary structure of an enzyme in that class of proteases. For example, a reference enzyme for carboxypeptidases is wheat carboxypeptidase (CPD-WII). The primary amino acid sequence and the crystal structure of CPD-WII are known (Liao and Remington, *J. Biol. Chem.*, 265:6528 (1990)) and can serve as reference points to identify equivalent amino acids in other carboxypeptidases.

The amino acid sequence and crystallographic structure of CPD-Y are known as well (Endrizzi et al., *Biochemistry*, 33:11106 (1994)) and can similarly be used as reference points to identify equivalent amino acids in other carboxypeptidases.

One method that is applied to identify residues in the active site of a protease with an unknown tertiary structure is comparison of the amino acid sequence of the protease of interest with the amino acid sequence of a homologous protease with a known tertiary structure. Thus, this method can be used to identify amino acids in the protease of interest that are equivalent to amino acids in the active site of the homologous protease. For example, see Olesen et al. *Protein Engineering*, 6:409 (1993). Alternatively, the amino acids in the active site can be identified by determination of the tertiary structure using X-ray crystallography or NMR techniques.

In a preferred version, carboxypeptidase Y is modified by substitution of amino acids in the active site. These amino acids are preferably found in the $S_1$ or $S_1'$ binding sites. Preferred amino acids of the $S_1$ binding site include Tyr147, Leu178, Tyr185, Tyr188, Asn241, Leu245, Trp312, Ile340 and Cys341. Preferred amino acids of the $S_1'$ binding site include Trp49, Asn51, Gly52, Cys56, Thr60, Phe64, Glu65, Glu145, Tyr256, Tyr269, Leu272, Ser297, Cys298 and Met398. Amino acids equivalent to these residues of the binding sites of carboxypeptidase Y are also preferred.

Amino acid substitutions in the $S_1$ binding site can preferably result in a mutant protease capable of transacylating a preselected substrate with a basic or acidic penultimate amino acid ($P_1$). Amino acid substitutions in the $S_1'$ binding site can preferably result in a mutant protease capable of performing transacylation reaction on preselected substrates with large apolar amino acid leaving groups and/or nucleophiles such as large apolar amino acids, proline and proline amide. The especially preferred enzyme is a customized carboxypeptidase that has different amino acid residues in a position equivalent to amino acid residue 178 or 398 of carboxypeptidase Y. A preferred substituent amino acid is serine at position 178.

The preferred customized protease is a carboxypeptidase that is capable of transacylating a preselected substrate having an acidic or basic amino acid such as growth hormone releasing factor with a C-terminal alanine (GRF (1–43)-Ala) (SEQ ID NO:2) and arginine as the penultimate amino acid. The especially preferred mutant carboxypeptidase catalyzes formation of growth hormone releasing factor with a leucine amide.

Selection can also involve choosing the different amino acid that will be substituted into the active site. While not meant to be a limitation of the invention, one way the amino acid to be inserted into the active site can be selected is by predicting the effect on the binding interaction between the preselected substrates and the customized protease. These substitutions can be conservative amino acid substitutions.

In general, the binding interaction between the substrate binding sites of the proteases and preselected substrate and/or nucleophile can directly affect the transacylation process. Although not intended to be a limitation of the invention, it is believed that the interactions between the amino acids of the binding sites and the amino acids of the substrate effect formation of the enzyme substrate complex (ES) which is a first step to transacylation. For serine or thiol proteases, enzyme substrate interactions lead to the formation of a tetrahedral transition state intermediate and subsequently to the cleavage of the peptide (ester) bond between the substrate core and leaving group. The resultant acyl- or thio-acyl species then undergoes nucleophilic attack (aminolysis) to form the transacylated product.

The binding interaction involved in formation of the ES complex include three major types: electrostatic interactions, hydrogen bonds, and van der Waal forces. Amino acid substitutions within the substrate binding sites can cause changes in the transacylation capabilities of the protease through changes in the binding affinity of an enzyme for a substrate (i.e. formation of ES complex), through modification of the interaction of the enzyme with the transition state as well as through interactions affecting the rate of competing aminolysis and hydrolysis reactions. Amino acid substitutions that affect each of these stages can be predicted based upon the preselected substrate with leaving group and the preselected nucleophile. The preferred substitutions include the substitution of Asn51 with glutamine and Leu178 with serine in carboxypeptidase Y.

The mutant or customized protease can also be a protease that exhibits enhanced transacylating capabilities. Enhanced transacylating capability can be determined by determining an increase in the yield of the transacylation product. Preferably, the increase in the yield is about 40 to 100% and more preferably about 80 to 100% increase over the yield catalyzed by the known protease. The preselected substrate can either be a substrate that can be transacylated by the known protease but at low yields (i.e., about 10–40%) or a substrate not substantially cleaved by the known protease (i.e., less than 10%).

B. Methods for Preparing Customized Protease

The method of the invention provides for preparing a customized protease derived from a known protease and that has a modified active site and that functions to alter the transacylation capability of the known protease. As used herein, the customized enzymes can be modified to transacylate a new substrate by mutating one of more amino acids in one or more of the substrate binding sites of a known protease. It is possible that mutation of as few as one amino acid in one substrate binding site can provide for transacylation of a substrate that was not a suitable substrate for the known protease. The active site can also be modified to provide an enzyme having enhanced transacylation capability, i.e., higher yields of transacylation.

Mutation of amino acids of the substrate binding sites can alter one or more functionalities which affect transacylation of a preselected substrate by a customized protease such as: (1) affinity of the customized protease for the core peptide portion of the substrate; (2) affinity of the customized protease for the leaving group or nucleophile; and (3) preference of catalysis of aminolysis over the competing hydrolysis reaction.

a. Providing a DNA Sequence of Known Proteases to be Mutated

According to a method of the invention, mutation of a known protease to produce a customized protease can be accomplished through site specific mutagenesis, random site mutagenesis and traditional mutagenesis. The first two methods require knowledge of the DNA sequence of known proteases and the location of codons which code for the substrate binding site amino acids. Amino acids in the active site of proteases are either known to those of skill in the art or can be identified by analogy to known proteases as described herein. The corresponding DNA sequence encoding the known protease and the location of codons for amino acids in the active sites are either known to those of skill in the art or can be derived from the amino acid sequence. For example, the DNA sequence and restriction map of the PRC1 gene which encodes carboxypeptidase Y (CPD-Y) (SEQ ID NO:32) and a source of the DNA sequence is described in Valls et al., *Cell*, 48:887–889 (1987). DNA sequences encoding known proteases can be obtained from an electronic database such as SwissProt, GeneBank, and EMBL. Once these sequences are identified, publications identifying vectors containing the DNA sequence can be located and used by those of skill in the art to prepare a customized protease.

If the DNA sequence and location of substrate binding sites is not available for a known enzyme, the putative DNA sequence can be derived from the amino acid sequence of the known protease. The amino acid sequence of the known protease can be used to prepare synthetic oligonucleotide probes. The probes can be used to identify DNA sequences encoding the known protease in suitable organisms by standard methods as described by Maniatis et al, *A Guide to Molecular Cloning* (1989). Once a DNA sequence encoding a known protease is isolated, codons corresponding to amino acids in the active site can be identified as described herein. Active site amino acids can be identified by comparing the primary or tertiary structure to other known active sites of other proteases or by X-ray crystallography as described herein.

b. Modifying Amino Acids in the Active Site

Amino acids in the active site can be modified by modifying the codon encoding the amino acids in the DNA sequence encoding the known protease. Amino acids in the active site and the location of codons encoding these amino acids are either known to those of skill in the art or can be determined using standard methods. Amino acids in the active site preferably include those found in the $S_1$, $S_1'$ or C binding sites. The codon or codons encoding amino acids of the active site of the protease are included in a targeted site on the DNA sequence. The targeted site includes the DNA sequence that is going to be mutated. One or more than one codon can be changed in the targeted site. Optionally, the targeted site can also include the DNA sequence surrounding the codon or codons for an amino acid in the active site. The DNA sequence of the targeted site surrounding the codon preferably includes about 3 to 9 nucleotides on either side of the codon or codons for amino acids in the active site. Modifications of codons include substitution, insertion or deletion of the codon.

The codons encoding amino acids of the active sites are preferably modified to encode a different amino acid than that of the known protease. In site specific modification, a selected amino acid in the active site can be changed either randomly or by substitution with a codon for a specific amino acid. In random site modification any number of codons can be modified by substitution with any number of amino acids. The modification of the codon results in a customized protease with altered transacylation capabilities.

The preferred codons for modification are those that encode amino acids in the $S_1$ or $S_1'$ binding sites of carboxypeptidases. While not meant to be a limitation of the invention, it is believed that modification of amino acids in the $S_1$ site can result in a mutant protease capable of transacylating a preselected substrate with a basic or acidic penultimate amino acid ($P_1$). Likewise, it is believed that a modification of amino acids in the $S_1'$ binding site can result in a mutant protease capable of transacylating a preselected substrate with an acidic or basic leaving group and/or amino acid amides as nucleophiles.

Choice of a specific amino acid substitution at a random or specific location can be based on the known or inferred mechanism of interaction of the binding site amino acid and the substrate. From this a rational inference is made, using knowledge of the properties of amino acids, of what amino acid substitution will provide the appropriate interaction to effect transacylation of the preselected substrate. Known amino acid properties which may be considered when selecting specific amino acid substitutions include electronic and steric factors. For example, specific amino acid substitution selection may be based on pKa values (of α-carboxyl and side chain hydrogens), amino acid side chain length, and amino acid side chain polarity at various pH. While not meant to be a limitation of the invention, the effect of the amino acid substitution can be predicted based upon the interactions involved in binding and catalysis as described herein for carboxypeptidase. Alternatively, if no data is available from which to make a rational inference of specific amino acid substitutions, random selection of amino acid substitutions can be made both with respect to the amino acids of the active site to be changed and the amino acid substitutions to be made.

According to the method of the invention, site specific and random site mutagenesis are used to mutate the known protease and can be accomplished through incorporation of an oligonucleotide containing a mutated or modified codon at the chosen or targeted codon location. Other methods of random and site specific mutagenesis can be employed as described by Maniatis, cited supra.

Preferred methods of incorporation of the oligonucleotide into the DNA sequence encoding the known protease to produce a modified DNA sequence include polymerase chain reaction (PCR) and standard cloning technology.

Oligonucleotides containing a mutated or modified codon can be obtained by standard methods. These standard methods include synthesis by automated methods. Methods for automated DNA synthesis are known to those of skill in the art. The synthetic oligonucleotides are comprised of a variable and a constant region and preferably are about 20 to 60 nucleotides long. The length of the oligonucleotide is dependent on two main factors; (1) the number of variable regions the oligonucleotide is coding for; and (2) the length of the constant regions.

The variable region of the oligonucleotide contains the nucleic acid codons which code for the mutated amino acids of the substrate binding sites. The codons for amino acids are known to those of skill in the art. The variable region of oligonucleotide can be designed to include a codon for a specific amino acid or any number of random amino acids. Therefore, the minimum number of codons in the variable region is three, which represents the codon for a single amino acid. The codons of the variable region correspond to the location of the codons to be mutated in the known protease. The variable region is flanked by the constant region of the oligonucleotide. If an oligonucleotide contains more than one variable region, there are constant regions between variable regions. The constant regions are necessary to incorporate the oligonucleotide into the customized protease gene and include codons corresponding to those of the known protease at that location (i.e., that are not mutated). The length of the constant region can depend on the means by which the oligonucleotide will be incorporated into the customized gene and the number of amino acid modifications included in the variable region. Preferably, the constant region includes about 3 to 50 nucleotides on either side of the variable region, and more preferably about 3 to 30 nucleotides on either side of the variable regions.

Once formed, the synthetic oligonucleotides are incorporated into the DNA sequence for the known protease in frame and at the targeted location. One way this insertion can occur is by cleavage with at least one appropriate restriction endonuclease so that the targeted site is deleted, followed by ligation of the synthetic oligonucleotide into the site that was deleted. Appropriate restriction endonucleases can be determined by examining the nucleotide sequence around the targeted site and by the size of the synthetic oligonucleotide to be inserted at the site. The recognition sequences of restriction enzymes are known to those of skill in the art, and an appropriate combination of enzymes can be readily selected by one of skill in the art.

In a preferred version, the codon for Asn51 of carboxypeptidase Y is modified to encode glutamine 51. The PCR1 gene encodes carboxypeptidase Y and can be obtained from plasmid pTSY3 which has been deposited with the American Type Culture Collection in Rockville, Md. on Oct. 26, 1993 and given Accession No. 75580. An oligonucleotide including a codon for glutamine at a site corresponding to the codon for Asn51 such as:

GGATCCGGTCATCCTTTGGTTGC̲A̲AGGGGGT (SEQ ID NO:4) (oligo N51Q)

(underline indicates changes to the codon at the targeted site) can be synthesized by automated DNA synthesis. The BamHI fragment of PRC1 includes the codon for amino acid 51. The DNA sequence of carboxypeptidase Y surrounding the codon for Asn51 can be deleted from the BamHI fragment of PRC1 with restriction endonucleases such as BstXI and SmaI. The synthetic oligonucleotide can then be introduced in place of the deleted DNA sequence at the SmaI-BstXI site of the BamHI fragment. The modified BamHI fragment is then inserted back into the entire DNA coding sequence for carboxypeptidase Y using known methods to form a modified DNA sequence. The sequence of the modified DNA sequence can be confirmed using dideoxy sequencing methodology.

Once the modified DNA sequence is obtained, it can be introduced into a suitable host cell, selected and expressed to yield the customized protease with the modified active site and that functions to alter the transacylation activity of the known protease.

The modified DNA sequence is preferably incorporated into a vector to provide for selection and expression. Suitable vectors include the yeast bacterial shuttle vectors YEp24, pRA21ΔBAM, pYSP1, pTSY3, pRA21, and pYSP32. The modified or mutated DNA sequence can be incorporated into the vectors by standard methods as described by Maniatis et al., cited supra, and Nielsen et al., *Appl. Microbiol. Biotechnol.,* 33:307 (1990).

Once combined with a vector, the vector is introduced into a suitable host cell for selection and expression. Suitable host sells include bacteria such as *E. coli* and yeast such as *S. cerevisiae*. Preferred host cells include *S. cerevisiae* strains having isogenic vp1 mutations, delta-prc1 mutations and ura3 mutations. Especially preferred hosts are *S. cerevisiae* strains that have vp1 mutations resulting secretion of active CPD-Y as described in Nielsen et al., cited supra.

The preferred vector is a plasmid pTSY3 which is the yeast bacterial shuttle vector YEp24 with a 3.2 kb DNA insert containing the PRC1 gene under the control of the PRC1 promoter. This plasmid has been deposited with the American Type Culture Collection, Rockville, Md., and given Accession No. 75580.

Suitable host cells are transformed by standard methods including transformation of calcium phosphate, calcium chloride or lithium acetate competent cells, microinjection, electroporation, and the like. Transformed cells can be selected based upon the presence of antibiotic resistance genes on the vector in the case of *E. coli* and based upon the presence of URA3 in the case of yeast. Transformed yeast cells can be screened for the production of mutant protease activity. Transformed yeast cells producing mutant proteases can be screened by detecting the ability of the transformed cells to hydrolyze a peptide substrate using standard methods as described by Nielsen et al., cited supra. Mutant proteases that can perform transacylation reactions with a preselected substrate and/or nucleophile can be further selected by assaying for transacylation activity by standard methods including those described in Examples 2 and 3.

Once the transformed cells are selected and amplified, mutant proteases can be purified using standard methods such as high performance liquid chromatography and affinity chromatography as described in Example 1.

In an alternative version, a novel method of the invention involves mutagenizing a known protease to form a customized protease having altered transacylating capability. The basic technique of the method involves in vitro DNA synthesis primed by mutagenic degenerate synthetic oligonucleotides. The method provides efficient screening of a large population of mutant transformants which eliminates the wild type background due to unmutagenized plasmids in the subsequent functional screens.

The steps of the method include providing a DNA sequence encoding a known protease. DNA sequences encoding known proteases are either publicly available or can be obtained by standard methods as described herein.

Once the DNA sequence encoding the known protease is obtained, one or more targeted sites are selected. A targeted site of the DNA preferably includes at least one codon for an amino acid of the active site to be modified as described herein. Once targeted sites are identified, the DNA sequence is modified at each targeted site by insertion of stop codons and optionally restriction endonuclease sites at the location to be mutated. Codons for stop codons are designated amber, ochre and opal, and the sequences of the stop codons are known to those of skill in the art. The DNA sequences recognized by a restriction endonuclease are known to those of skill in the art. The DNA sequence including the restriction endonuclease site can be adjacent to the stop codon or it can overlap with the stop codon. The oligonucleotide sequence inserted at the target site can be prepared by standard methods including automated DNA synthesis.

The inserted oligonucleotide sequence is preferably about 3 to 60 nucleotides long and can be inserted into one or more targeted site using standard methods such as in vitro DNA synthesis as described by Maniatis et al, cited supra. Once the oligonucleotide having a stop codon and optionally restriction endonuclease site is inserted into a targeted site of the DNA encoding the known protease, a modified DNA sequence encoding an inactive known protease is formed. The presence of stop codons results in the expression of truncated forms of the known protease lacking activity.

The DNA sequence encoding an inactive known protease is introduced into a vector, preferably a phagemid vector. The vector is transformed into suitable host cells such as *E. coli* for amplification. Once amplified, the vector is isolated and single stranded DNA can be prepared. Optionally, the DNA sequence can be introduced into a vector carrying an inactive antibiotic resistance gene such as a gene encoding ampicillin resistance that has a frameshift mutation. A preferred phagemid vector is the pYSP1.

A mutant DNA strand encoding the customized protease can be synthesized by incubating the single stranded DNA with one or more first degenerate oligonucleotides in the presence of DNA polymerase and DNA ligase. A first degenerate oligonucleotide has variable and constant regions as described previously herein. The variable region of a degenerate oligonucleotide includes at least one mutated codon for an amino acid in the active site of the known protease and that has been targeted. The mutated codon is found at the same location with respect to the surrounding DNA as the codon for the amino acid in the known protease. An oligonucleotide is degenerate if the mutated codons are randomly changed to encode any one of the 20 amino acids. A degenerate oligonucleotide at the mutated codon has the sequence of NNN wherein N corresponds to any one of the four nucleotides. A degenerate oligonucleotide preferably includes about 10 to 50 nucleotides on both sides of the mutated codon. The codons of the constant region correspond to the codons of the known protease at the targeted location in the known protease. Degenerate oligonucleotides can be for any of the 20 amino acids and are randomly generated using known methods and as described in Olesen et al., cited supra.

When the DNA sequence encoding the known protease contains more than one targeted site that has been modified by stop codons and/or restriction endonuclease sites, it may be desirable to synthesize a mutant DNA strand that is modified at only one or some of the targeted sites. When mutation is desired only at some of the targeted sites having stop codons, the other targeted sites in the mutant enzyme should have the sequence of the known enzyme at these other targeted sites. One or more second oligonucleotides can be included in the DNA synthesis mixture that function to ensure that the other targeted sites that are not to be mutated in the mutant DNA strand have the sequence of the known enzyme as described in Olesen et al., cited supra. The second oligonucleotides include codons corresponding to those in the known protease that have been replaced by stop codons and optionally restriction endonuclease sites at targeted sites. Each second oligonucleotide has the same sequence at a specific targeted site as the known protease. A second oligonucleotide preferably has about 20 to 60 nucleotides.

The synthesis mixture can also optionally include an oligonucleotide that provides for repair of an antibiotic resistance gene. When the DNA sequence encoding the known protease is inserted into a vector, that vector preferably includes a mutated antibiotic resistance gene such as ampicillin resistance. Including one or more oligonucleotides that can repair the mutation of the antibiotic resistance gene in the DNA synthesis mixture results in a mutant DNA strand that has a functional antibiotic resistance gene. An oligonucleotide that can repair the antibiotic resistance gene includes codons that provide for the correct DNA sequence at the relevant mutation in the resistance gene. These oligonucleotides are known to those of skill in the art or can be prepared by standard methods as described in herein.

Once synthesis of the mutant DNA is complete, desirable mutant enzymes encoded by the DNA can be selected and screened for the ability to act on a preselected substrate for alteration of transacylation capability. The mutant DNA can be selected and amplified first in a suitable host cell such as *E. coli* followed by introduction into a suitable host cell that can secrete proteases such as *S. cerevisiae* strains. Selection methods for transformed cells include selecting for antibiotic resistance based upon the presence of an antibiotic resistance gene on a vector. Methods for selection in yeast using selectable marker genes are known to those of skill in the art.

Transformed cells can be screened to identify cells having the customized protease with the desired functional activity. The desired customized protease can include a protease that can hydrolyze a preselected substrate having an acidic or basic penultimate amino acid, a protease that can catalyze transacylation reaction in which a preselected substrate is modified by a preselected nucleophile, and a protease with enhanced transacylation capabilities. The preferred customized protease is a carboxypeptidase that can modify a preselected substrate with a basic penultimate amino acid with a terminal leucine amide. One or more screening and selecting methods can be employed.

For example, mutant enzymes capable of hydrolyzing a preselected substrate are first selected and screened for hydrolysis activity and then those selected mutants are screened for transacylation activity. Substrate hydrolysis is used as a first level selection to ensure that the mutant is capable of acting on the preselected substrate. The mutant enzymes capable of hydrolyzing the preselected substrate are then further screened for transacylating capability. Selection of transformants expressing hydrolysis activity of the preselected substrate can be performed using the plate activity method or the color overlay method. For detection of low level customized proteases, the color overlay method is preferred.

According to the invention, transformed cells expressing customized proteases can be selected for preselected substrate hydrolysis activity using a plate activity method. This method of the invention utilizes a bacterial or yeast host cell which requires an amino acid for growth. The amino acid required for growth is provided to the transformed host cells as a C-terminal amino acid of a peptide. By culturing the transformants on a media deficient in the leaving group amino acid, only those transformants capable of releasing the leaving group from the peptide substrate can grow. This method is described in Olesen et al., *Protein Eng.*, cited supra. For example, a vps strain of *S. cerevisiae* which requires Leu for growth is used to select for transformants expressing a mutant CPD-Y gene capable of cleaving a terminal Leu from a preselected substrate such as N-blocked-X-Leu-OH dipeptides (X=Glu, Gly, Ser, His, Pro, Trp, or Lys). Only cells which express a protease which can release the terminal Leu from these substrates can grow on these plates.

A preferred method for selection of transformants which express a customized protease capable of hydrolyzing a preselected substrate is the color overlay method. According to this method, transformant colonies are overlaid by agar containing a chromogenic substrate which reveals customized protease activity. The chromogenic substrate turns color upon reaction with the product formed by catalytic action of the customized protease. In a preferred version, the transformed cells are incubated with a preselected peptide or amino acid substrate. The preselected peptide or substrate such as N-acetyl-L-alanine β-naphthyl ester is acted upon by transformed cells expressing a customized protease and the reaction product is detected by simultaneously overlaying the transformed cells with a chromogenic agent such as Garnet Red that changes colors upon exposure to the reaction products.

Customized proteases which have been mutated and screened for the capacity to act on a preselected substrate can be further screened for transacylation capability. One method that can be employed to screen for transacylation capability is that described in Examples 2 and 3. Customized proteases are purified from the transformed cells by methods known in the art and as described in Examples 2 and 3. The purified customized protease is mixed with the preselected substrate under conditions favorable for transacylation such as pH of about 7 to 9.5 and in the presence of a suitable nucleophile. Transformants which produce customized proteases capable of catalyzing transacylation of the preselected substrate can be identified by following the appearance and/or amount of the desired reaction product by standard methods.

In a preferred version, the PRC1 gene encoding carboxypeptidase Y is modified by insertion of DNA sequences at target sites as follows:

```
TAA GCT TCC      (SEQ ID NO:5) at Tyr147         ochre stop codon
   HindIII TGAATTCCT        (SEQ ID NO:6) at Leu178         opal stop codon
   EcoRI TAG CCCGGG TGT   (SEQ ID NO:7) at Glu214, Arg216 amber
stop codon
      SmaI TAA ATCGAT ACC   (SEQ ID NO:8) at Ile340, Cys341 ochre
stop codon
      ClaI
```

The target sites in carboxypeptidase were selected based on homology to carboxypeptidase-WII. The modified DNA sequence encodes an inactive carboxypeptidase Y. The DNA sequence as modified is amplified as phagemid vector pYSP32 in E. coli. The preferred vector also contains an inactive frame shifted ampicillin resistance gene. Single stranded DNA of pYSP32 can be generated by standard methods.

The single stranded DNA can be incubated with up to four first degenerate oligonucleotides, each 20 to 60 nucleotides long and containing degenerated codons at the center. A preferred first degenerate oligonucleotide for position 178 includes the sequence:

GGC NNN ACT wherein NNN is situated at the center of the oligonucleotide and corresponds to the location of the codon for amino acid 178. NNN is a codon for any of the 20 amino acids. Degenerate oligonucleotides can be synthesized by automated synthesis.

One or more second oligonucleotides can be included in the preferred synthetic mixture and in which case they each replace one of the first oligonucleotides. The second oligonucleotide includes codons for amino acids at positions 147, 178, 215 and 216, and 340 and 341 of carboxypeptidase Y, as follows:

```
TCC TAC GCC      (SEQ ID NO:9)    Tyr147

TTG GAA CGT TGT  (SEQ ID NO:10)   Glu215, Arg216

TTC ATC TGT ACC  (SEQ ID NO:11)   Ile340, Cys341

GGC CTC ACT      (SEQ ID NO:12)   Leu178
```

The presence of these second nucleotides ensures the mutant DNA strand is synthesized without stop codons at other targeted sites. One preferred mutagenesis mixture contains a first degenerate oligonucleotide for position 178 and a second oligonucleotide for each position of Tyr147, Glu215, Arg216, Ile340 and Cys341.

Optionally, the preferred DNA synthesis mixture also contains one or more third oligonucleotides, ampicillin repair oligonucleotides. The repair oligonucleotides provide for synthesis of a mutant DNA sequence having a functional ampicillin resistance gene operably linked to the DNA sequence encoding the mutant or customized protease.

The mixture of single stranded DNA and oligonucleotides is incubated in the presence of precursor nucleotides, DNA polymerase and DNA ligase. Mutant DNA sequences encoding the customized protease are formed and can optionally be linked to a functional ampicillin resistance gene. The mutant DNA is introduced into a suitable mismatch repair deficient bacteria for amplification and selection and subsequently introduced into yeast for screening. The preferred suitable yeast cell is a S. cerevisiae strain that has a vps mutation, and/or requires at least one amino acid for growth. Especially preferred S. cerevisiae strains include W2579, K2579LLR and JHRY20-2CΔ3.

The transformed E. coli cells can be selected first for the ability to grow in the presence of ampicillin. Subsequently, transformants are further selected for the ability to grow on a medium deficient in the amino acid required for growth and in the presence of the peptide substrate containing the amino acid for growth at the C-terminus. For example, a host cell that cannot normally grow without leucine is transformed with mutant DNA and plated onto leucine deficient medium supplement with a preselected peptide having the following formula:

$P_n P_1$-A where A is leucine and $P_1$ is an amino acid not sufficiently acted on by known protease such as any one of Glu, Gly, Ser, His, Pro, Trp or Lys. Transformants that can grow on leucine deficient medium supplement with a preselected polypeptide such as $P_n$-Lys-Leu can act on the preselected polypeptide to release leucine, thereby providing a source of leucine for growth. These expressed proteases are then screened for the ability to transacylate a preselected polypeptide such as $P_n$-Arg-Ala where $P_n$ is growth hormone releasing factor and leucine amide.

Customized proteases which favor aminolysis over hydrolysis can be produced using traditional mutagenesis. According to this method of the invention, mutation of the amino acid composition of a known protease is accomplished by subjecting DNA or cells containing a vector encoding a DNA sequence for known protease to a mutagenic agent such as UV light, nitrosoguanidine, ethylmethyl sulfonate, bisulfite, dimethyl sulfate, formic acid, hydrazine, hydroxylamine, methoxylamine, nitrous acid, potassium sulfate, and others. Methods of traditional mutagenesis are known in the art and are described, for example: for chemical in vitro mutagenesis: Myers et al., *Science*, 229:242–247 (1985); Hayatsu, *Methods Enzymol.*, 45:568–587 (1976); Shortle et al., *Methods Enzymol.*, 100:457–568 (1983); Kadonga et al., *Nucl. Acids. Res.*, 13:1733–1745 (1985); Busby et al., *J. Mol. Biol.*, 154:197–209 (1982); and Loeb, *Cell*, 40:483–484 (1985); for nucleotide misincorporation: Kornberg, *DNA Replication*, Freeman, San Francisco (1980) at page 724; and Kunkel et al., *J. Biol. Chem.*, 254:5718–5725 (1979); for incorporation of nucleotide analogs: Flavel et al., *J. Mol. Biol.*, 89:255–272 (1974); Dierks et al., *Cell*, 22:659–706 (1983)1 Dodson et al., *PNAS*, 79:7440–7444 (1982); Eadie et al., *Nature*, 308:201–203 (1984); Grossberger et al., *PNAS*, 78:5689–587 (1981); and Mott et al., *Nucl. Acids Res.*, 12:4139–4152 (1984).

The mutated vectors are then incorporated into a suitable expression system and the expressed customized enzymes are selected and screened. The methods for selecting and screening customized protease produced by traditional mutagenesis can be performed as described above for transformants produced by site specific and random site mutagenesis. Plate activity and color overlay selection can be utilized to select for those transformants which express a customized protease capable of acting on a preselected substrate. Those customized proteases capable of acting on a preselected substrate are purified and mixed with a preselected substrate and nucleophile under conditions favorable for transacylation to screen for enzymes capable of catalyzing the transacylation of the preselected substrate.

C. Method of Transacylating Substrates Using Customized Proteases

The invention also provides a method for using the customized enzyme to transacylate a preselected substrate with a preselected nucleophile. This method is useful to add nucleophiles such as D-amino acids, modified amino acids and radiolabelled amino acids to the termini of recombinantly produced peptides to form transacylation products. This method can also be applied to naturally occurring or synthetic peptides to form useful analogs or derivatives.

The customized protease of the invention is designed to either enhance transacylation capabilities (i.e., yields) or act on a preselected substrate and/or nucleophile poorly accepted by the known proteases. The customized protease can be prepared and selected by the methods described herein. The preselected substrate is selected depending on the desired transacylation product. The preselected substrate is preferably not substantially transacylated by the known proteases. "Substantially" in this context means that the yields of transacylation with the preselected substrate and with a particular nucleophile are preferably about 0 to 10% under standard conditions. The preselected substrate preferably has a basic or acidic amino acid as the penultimate amino acid. The preferred amount of the preselected substrate depends on the substrate specificity of the enzyme for the substrate as well as the solubility of the substrate in the chosen solvent and is about 0.2 to 10 mM. A preselected substrate can be a naturally occurring peptide, a synthetic peptide or a recombinantly produced peptide.

The preselected nucleophile is preferably not an effective-nucleophile with the known protease. The nucleophiles are preferably amino acids, radioactively labelled amino acids, and amino acid amides. Nucleophiles can be prepared by standard synthetic methods known to those of skill in the art such as described in Breddam et al., *Int. J. Peptide Res.*, 37:153–160 (1991). A preferred amount of a nucleophile also depends on the affinity of the enzyme and solubility of the nucleophile in the chosen solvent and is about 10 mM to 2M.

Reaction conditions resulting in high yields of the desired product can vary with a given enzyme substrate system. Reaction conditions can be altered to minimize degradation and polymerization of the products. Such side reactions may, when using ester substrates together with a serine carboxypeptidase, be avoided by increasing the pH above 8.0 when aqueous solvents are employed. Alternatively, side reactions can be avoided by conducting the reaction in an organic solvent.

Transacylation can be performed in aqueous buffer solution. Preferred buffer solutions include 50 mM HEPES and 5 mM EDTA, pH 7.5 or 50 mM CHES and 5 mm EDTA, pH 9.5. It is of importance that the chosen buffer is unable to act as a nucleophile in the transacylation reaction. The preferred pH for transacylation using an alcohol leaving group is preferably about pH 6.5 to 9.5 and more preferably pH 7.5 to 8.5. The preferred pH for transacylation using an amino acid or peptide derivative leaving group is preferably about pH 5.5 to 8.5, and more preferably about preferably pH 6.5 to 7.5.

The production of the transacylation product is monitored by HPLC or other appropriate analytical technique. The reaction can be stopped by addition of an acidic solution to bring the pH of the reaction mixture down to about pH 1 to 3. Alternatively, the reaction can be stopped by addition of an enzyme inhibitor such as phenyl methane sulfonyl fluoride (PMSF), or diisopropyl phosphoryl fluoridate (DFP). The transacylation product can be separated from the reaction mixture by reverse phase chromatography, hydrophobic interaction chromatography, ion exchange chromatography, or HPLC.

Alternatively, the transacylation reaction can be performed in organic solvents for those enzymes substrate systems capable of functioning in organic solvents. Suitable organic solvents for the transacylation reaction include dimethyl sulfoxide (DMSO), N,N'-dimethylacetamide and other similar solvents. The methodology for transacylation in organic solvents is described in Bongers et al., *Int. J. Peptide Protein Res.*, 40:268 (1992).

In a preferred example for transpeptidation using an amino acid leaving group in aqueous solution, the preselected peptide substrate, GRF (1–43)-Ala (SEQ ID NO:2), is dissolved in a 5% solution of acetic acid. The nucleophile, leucine amide, is dissolved in 50 mM HEPES, 5 mM EDTA to a final concentration of 500 mM. 25 $\mu$l of a 40 mM solution of GRF (1–43)-Ala (SEQ ID NO:2) is added pr. 950 $\mu$l of nucleophile solution and the pH is add to 7.5 at 20° C. The customized protease is added to the mixture in 25 $\mu$l of water pr. ml solution, resulting in an enzyme concentration of about 0.002 to 0.07 mg/ml. The reaction is followed by HPLC and is stopped when no additional product is formed by the addition of one volume of 2.5% trifluoracetic acid.

EXAMPLE 1

Site Specific Mutagenesis of Carboxypeptidase Y Active Site

The three-dimensional structure of carboxypeptidase Y suggests that the side chains of Trp49, Asn51, Gly52, Cys56, Thr60, Phe64, Glu65, Glu145, Tyr256, Tyr269, Leu272, Ser297, Cys298 and Met398 are important in the active site of the enzyme. These amino acid residues were mutated by site specific mutagenesis to form enzymes with single, double, or triple mutations.

The following mutants of carboxypeptidase Y have been constructed using standard methods:

Asn51 has been replaced with:
  Alanine (N51A)
  Cysteine (N51C)
  Glycine (N51G)
  Valine (N51V)
  Aspartic Acid (N51D)
  Glutamic Acid (N51E)
  Glutamine (N51Q)
  Serine (N51S)
  Threonine (N51T)

Glu 65 has been replaced by:
  Alanine (E65A)
  Glutamine (E65Q)

Glu145 has been replaced by:
  Alanine (E145A)
  Glutamine (E145Q)
  Serine (E145S)
  Asparagine (E145N)
  Aspartic Acid (E145D)

Trp49 has been replaced by:
  Phenylalanine (W49F)

In addition, enzymes having more than the mutation as shown below have been constructed:

N51A+E145A

E65A+E145A

NS1A+E65A+E145A

E65Q+E145Q

The general methodology used to construct the mutant enzymes is by site specific mutagenesis using the polymerase chain reaction.

For example, a plasmid pUC-α30 was constructed by inserting a 1112 bp BamHI fragment of the PRC1 gene from pYTS3 containing the coding region for all amino acid residues involved in the formation of the active site into the unique BamHI site in the polylinker of pUC19. Yanisch-Perron et al., *Gene*, 33:103 (1985); Stevens et al. *Yeast Cell Biology*, Ed. J. Hicks, New York, Alan R. Liss, at pages 519–536 (1986). The orientation of the fragment was opposite of the lacZ gene. pUC-α30 contains unique BstXI, EcoRI, NaeI and SmaI restriction sites which can be used in cloning and mutagenesis procedures.

The mutations W49F and N51A were made by the polymerase chain reaction (PCR) (Innes et al., 1990) in a Perkin Elmer Cetus DNA Thermal Cycler using a Gene Amp kit (Perkin Elmer Cetus) on pUC-α30 with GTTTCTGTCCT-TGTGAGACAAAATTTCAGA (SEQ ID NO:13) (oligo wtl1) and with either GGATCCGGTCATCCTTT TCTTGAACGGG (SEQ ID NO:14) (oligo W49F) or GCAAAGGATCCGGTCATCCTTTGGTTG GCAGGGGCCA (SEQ ID NO:15) (oligo N51A). Nucleotides underlined are different from wild-type. Cleavage with BstXI allowed insertion of the PCR fragment into a SmaI-BstXI vector fragment of pUC-α30.

The mutation E145A was made by PCR with GCAAG-GCGATTAAGTTGGGT (SEQ ID NO:16) (oligo pUC19 sp1) and GGCGTAGGAAGCCCCAGCGAT (SEQ ID NO:17) (oligo E145A) on pUC-α30. Cleavage of the PCR fragment with EcoRI allowed introduction into a NaeI-EcoRI vector fragment of pUC-α30.

The mutations E65A and N51A+E65A were produced by fusion of two overlapping PCR fragments using either pUC-α30 or pUC-α30-N51A as template. Fragment 1 was generated with CTGTTCTTTGCATTAGGACCC (SEQ ID NO:18) (oligo E65A) and (oligo wt1) and fragment 2 with (oligo pUC19sq1) and (oligo E145A). An additional PCR reaction was performed on the fused fragment with oligo pUC19sq1 and oligo wt1. The resultant fragment was cut with EcoRI and BstXI, thus, removing the unwanted mutation on position 145, and ligated into a pUC-α30 vector fragment cut with the same restriction enzymes.

N51A+E145A, E65A+E145A, and N51A+E65A+E145A were made by proper combination of the above listed mutations exploiting the EcoRI site in the polylinker and exploiting that BstXI cleaves between position 65 and 145.

The mutated sequences were introduced into the PRC1 gene by transferring the mutated 1112 bp BamHI fragment into the vector pRA21ΔBam. The fragment inserted into pRA21ΔBam was controlled for the absence of any non-silent secondary mutation by sequencing using the Taq Dye-Dideoxy™ terminator cycle sequencing kit and the model 373A DNA-sequencing system from Applied Biosystems, USA.

Site directed mutagenesis on position 51 and 145 was performed using polymerase chain reaction and restriction endonuclease cleavage as described herein. The following oligonucleotides were used in the mutagenesis reactions:

GCAAAGGATCCGGTCATCCTTTGGTTGGACGGGGCCA (SEQ ID NO:19) (oligo N51D),

GGATCCGGTCATCCTTTGGTTGGAAGGGGCCA (SEQ ID NO:20) (oligo N51E),

GGATCCGGTCATCCTTTGGTTGCAGGGGGT (SEQ ID NO:21) (oligo N51Q),

GGATCCGGTCATCCTTTGGTTGAGTGGGGGT (SEQ ID NO:22) (oligo N51S),

GGATCCGGTCATCCTTTGGTTGACTGGGGGT (SEQ ID NO:23) (oligo N51T),

GGCGTAGGAATCCCCAGCGAT (SEQ ID NO:24) (oligo E145D),

GGCGTAGGAATTCCCAGCGAT (SEQ ID NO:25) (oligo E145D)

GGCGTAGGATTGCCCAGCGAT (SEQ ID NO:26) (oligo E145Q),

GGCGTAGGATGACCCAGCGAT (SEQ ID NO:27) (oligo E145S).

Underlined nucleotides are different from wild-type. All fragments generated by the PCR reaction were ligated into pUC-α30 after cleavage with the appropriate restriction enzymes such as EcoRI (E145) or BstXI (Asn51). The absence of any non-silent secondary mutation was confirmed by sequencing using the Taq Dye-Dideoxy™ terminator cycle sequencing kit and the model 373A DNA-sequencing system from Applied Biosystems, USA.

The mutant enzymes containing cysteine (N51C), valine (N51V), or glycine (N51G), glutamine (E65Q), and asparagine (E145N) were prepared in a similar manner.

Once the DNA sequence encoding the PCR enzyme was mutated as described herein, it was transferred into the vector pRA21ΔBam. This vector was then introduced into S. cerevisiae strain (W2579(prcΔLEU2 ura 3-51, pep 4-3) as described by Ito et al. *J. Bacteriol.*, 153:163–168 (1983) using lithium acetate. The stability of plasmids in stationary-phase yeast cells was determined by plating culture samples on YPD medium (1% yeast extract [Difco], 2% peptone [Difco] and 2% glucose) and subsequent replica-plating of about 100 colonies to SC medium lacking uracil. Yeast cultures were grown in MU/pro medium plus 50 mM potassium phosphate.

Mutant enzymes were purified from a one liter culture grown under the conditions previously described. (Nielsen et al., 1990). Growth media containing secreted mutant enzyme was adjusted to pH 4.4 with concentrated acetic acid and then directly applied to the GYBS-Sepharose affinity column according to the procedure of Johansen et al. (1976). N51A, which did not bind effectively to GYBS-Sepharose, was subjected to diafiltration against 10 mM $NaH_2PO_4$, pH 7.0, using a Pellicon system (Millipore) and then purified by ion exchange chromatography on a DEAE Fractogel 650 column (2.6×6 cm). The column was washed until $A_{280}$ was below 0.01 and elution was accomplished with a linear salt gradient from 0 to 0.5 M NaCl in 10 mM $NaH_2PO_4$, pH 7.0. The elute was concentrated using an Amicon cell and applied to a Sephacryl-S300 column (1 cm×100 cm) equilibrated with 50 mM $NaH_2PO_4$, pH 7.0. Fractions with constant specific activity were pooled, concentrated and dialyzed against water. All enzyme preparations were stored frozen in water at −18° C.

The purity of the mutant enzymes was ascertained by SDS-PAGE on 12.5% homogeneous gels using the Phast-System from Pharmacia. The concentration of CPD-Y mutants was determined spectrophotometrically using $A_{280}$ (1 mg/ml=1.48) (Johansen et al., (1976) cited supra).

Once prepared, the mutant or customized enzymes can be evaluated for a change in the transpeptidation reaction.

EXAMPLE 2

Carboxypeptidase Y Mutants With Improved Characteristics in Transacylation Reactions Using Amino Acids as Nucleophiles The binding site in carboxypeptidase Y (CPD-Y) for the negatively charged C-terminal carboxylate group of peptide substrates has been identified using site directed mutagenesis as described herein. While not meant to be a limitation of the invention, it is believed that the carboxylate group of the peptide substrate binds to the side chains of Asn51 and Glu145 in the $S_1'$ binding pocket. Both side chains can act as hydrogen bond donors. The side chains of Asn51 and Glu145 appear to be oriented by hydrogen bonds with Glu65 and Trp49 which, therefore, have an indirect function in the binding of the carboxylate group of peptide substrates.

Serine carboxypeptidases also catalyze the hydrolysis of peptide esters and this activity increases with pH and remains constant in the pH range 7 to 9.5. Thus, at basic pH, the esterase activity is high and the peptidase activity is low. These unique properties, combined with an ability to catalyze transacylation reactions with amino acids or amino acid derivatives as nucleophiles, suggest that serine carboxypeptidases can be useful in peptide synthesis. However, many substrates and nucleophiles cannot be catalyzed by known enzymes. With amino acid methyl esters as nucleophiles, medium yields (40–80%) are obtained but this method is complicated by the risk of further elongation of the product (oligomerization). It would be valuable to use amino acids rather than amino acid amides as nucleophiles.

It has been demonstrated that mutant carboxypeptidase enzymes can bind to and catalyze peptide elongation with amino acids as nucleophiles in higher yields. With amino acids as nucleophiles, yields exceeding 60% are obtained in a few cases but yields of 10–40% are much more common and H-Pro-OH, H-Glu-OH and H-Asp-OH are not accepted as nucleophiles. Thus, the yields obtained with amino acids as nucleophiles are rarely satisfactory. The low yields with amino acids as nucleophiles are not due to degradation of the product since the reaction is carried out at basic pH where the peptidase activity is very low (see above), thus, securing accumulation of the peptide product in the reaction mixture.

Mutants of carboxypeptidase Y were examined for the capacity to transacylate certain substrates using amino acids as nucleophiles. Some amino acid substitutions in the active site of mutant carboxypeptidase Y enzymes were also made knowing that they were not likely to improve the yields of transacylation reactions, but rather to investigate the mechanism of action of the binding and catalysis with certain types of nucleophiles.

CPD-Y was obtained from Carlbiotech, Copenhagen, Denmark. Amino acids and buffers were from Bachem, Switzerland or Sigma, USA. The mutants E65A, E65Q, E145A, E145Q, E61A+E145A, E65Q+E145Q, N51S, N51Q, N51A, and N51A+N145A were prepared as described in Example 1. The purity of the enzymes was ascertained by SDS polyacrylamide gel electrophoresis.

Aminolysis reactions were carried out in the following way. The nucleophile was dissolved in 50 mM Hepes, 5 mM EDTA and pH was adjusted to 7.5. Five (5) μl of substrate (8 mM FA-Ala-OBzl in methanol) was added to 190 μl nucleophile solution followed by 5 μl enzyme, resulting in a substrate concentration of 0.2 mM. For reactions carried out at pH 9.5, Hepes was replaced with Ches. During the reaction, 20 μl aliquots were removed from the reaction mixture and added to 50 μl 1% trifluoroacetic acid to quench the reaction. The reactant composition was determined by HPLC using a Waters HPLC equipped with a C-18 Waters Novapac 4μ reverse phase column and various gradients of acetonitrile in 0.1% trifluoroacetic acid. The separation was monitored at 302 nm allowing the direct quantification of the products from the integrated peak areas. The composition of the reaction mixture was determined at least twice during the reaction, the first time when 20–50% (preferably 35%) of the ester substrate had been consumed in the reaction and the second time when 50–90% (preferably 80%) of the substrate had been consumed. The products were collected and identified by amino acid analysis after acid hydrolysis using a Pharmacia Alpha Plus analyzer.

Further identification was obtained by co-chromatography of authentic standard compounds. The fraction of aminolysis (fa) was expressed as the ratio between the formed aminolysis product and the sum of all products being formed, i.e., unconsumed substrate was disregarded in the calculations. The $K_{N(app)}$, representing the nucleophile concentration at which fa is half the maximum value (a measure for the dissociation constant of the nucleophile), and $fa_{max}$ (the highest possible fa obtained at saturation of the enzyme with nucleophile) were determined by fitting the values of fa obtained at a minimum of seven concentrations of nucleophile to a saturation. The value of fa obtained at the highest possible nucleophile concentration is designated $fa_{sat}$.

The ability of CPD-Y to catalyze transacylation reactions with amino acids or amino acid derivatives acting as nucleophiles in competition with water can be studied. A study of the beneficial effects of structural alterations within the $S_1'$ binding site on the productive binding of amino acids to effect aminolysis is preferably performed with an ester substrate. Transacylation reactions should preferably be performed at slightly basic pH to maximize the esterase activity and minimize the peptidase activity. When amino acids are used as nucleophiles the product peptide is very slowly degraded by the enzyme and, as a consequence, it accumulates in the reaction mixture, FA-Ala-OBzl is hydrolyzed at very high $k_{cat}/K_M$ by CPD-Y and the prepared mutant enzymes allowing the use of low concentrations of enzyme (0.5 µg/ml). The fact that the peptide products are hydrolyzed at much lower $k_{cat}/K_M$ prevents degradation of the aminolysis product. At pH 7.5, with H-Val-OH as added nucleophile, two products were formed: FA-Ala-OH (hydrolysis) and FA-Ala-Val-OH (aminolysis). At each concentration of nucleophile, the fraction undergoing aminolysis reaction was constant with time and independent of the concentration of substrate remaining in the reaction mixture. This indicates that the product FA-Ala-Val-OH is not hydrolyzed by the enzyme under the employed reaction conditions and, thus, the ratio of the two products reflect the relative rates of the two competing reactions. With increasing concentrations of H-Val-OH, fa increased but it did not exceed 0.32. The correlation between the fraction of aminolysis and concentration of H-Val-OH was unaffected by the presence of 0.5 M NaCl in the reaction medium. Hence, the ratio of rates of the hydrolysis and aminolysis reaction is independent of the ionic strength of the reaction medium.

The observation that CPD-Y becomes saturated with H-Val-OH is consistent with the previous demonstrations that nucleophiles bind to the acyl-enzyme intermediate of serine carboxypeptidases prior to the deacylation reaction. The correlation between fa and the concentration of nucleophile is consistent with $K_{N(app)}$ and $fa_{max}$ values of 13 mM and 0.32, respectively. The reaction was also carried out at pH 9.5 and the values for $K_{N(app)}$ and $fa_{max}$ were 19 mM and 0.31, respectively, suggesting that the ratio of the two forms of the nucleophile (amino/ammonium) has little influence on the synthesis parameters.

The influence of the side chain of the amino acid nucleophile on $fa_{max}$ and $K_{N(app)}$ was investigated. $K_{N(app)}$ decreased in the following order:

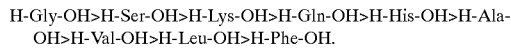

H-Gly-OH>H-Ser-OH>H-Lys-OH>H-Gln-OH>H-His-OH>H-Ala-OH>H-Val-OH>H-Leu-OH>H-Phe-OH.

(See Table I). With H-Pro-PH and H-Glu-OH, no aminolysis product was obtained. Thus, hydrophilic amino acids bind much less efficiently than hydrophobic ones. The highest $fa_{max}$ values were obtained with the amino acids that bind the least efficient: with H-Gly-OH, H-Ala-OH, H-Ser-OH, and H-Arg-OH, the $fa_{max}$ values exceeded 0.8, whereas with the hydrophobic and efficiently binding H-Val-OH, H-Leu-OH and H-Phe-OH, values below 0.4 were obtained.

TABLE I

CPD-Y Catalyzed Aminolysis of an Ester Substrate
Using Amino Acids as Nucleophiles
The Influence of Amino Acid Structure on
the Parameters for the Aminolysis Reaction

| Nucleophile | $fa_{sat}$ | $fa_{max}$ | $K_{N(app)}$ |
| --- | --- | --- | --- |
| H—Gly—OH | 0.60 | 0.92 ± 0.01 | 1500 ± 50 |
| H—Ser—OH | 0.78 | 0.87 ± 0.01 | 310 ± 20 |
| H—Lys—OH | 0.79 | 0.81 ± 0.03 | 190 ± 30 |
| H—His—OH | 0.20 | 0.27 ± 0.01 | 87 ± 9 |
| H—Gln—OH | 0.64 | 0.90 ± 0.02 | 150 ± 8 |
| H—Glu—OH | 0 | n.d. | n.d. |
| H—Ala—OH | 0.85 | 0.91 ± 0.02 | 83 ± 7 |
| H—Val—OH | 0.30 | 0.32 ± 0.01 | 13 ± 1 |
| H—Leu—OH | 0.32 | 0.35 ± 0.01 | 10 ± 1 |
| H—Phe—OH | 0.14 | 0.15 ± 0.01 | 9.5 ± 1 |
| H—Pro—OH | 0 | n.d. | n.d. |

All reactions were performed at pH 7.5 as described herein. The values for $K_{N(app)}$ are in mM. The concentrations at which $fa_{sat}$ was obtained were: H—Gly—OH = 2.9M, H—Ser—OH = 3.2M, H—Lys—OH = 2.7M, H—His—OH = 0.25M, H—Gln—OH = 0.37M, H—Glu—OH = 1.1M, H—Ala—OH = 1.4M, H—Val—OH = 0.48M, H—Leu—OH = 0.14M, H—Phe—OH = 0.14M and H—Pro—OH = N.D.

With amino acid amides as nucleophiles, $fa_{max}$ consistently exceeds 0.85 and is essentially independent of the hydrophobicity of the side chain.

While not meant to be a limitation of the invention, the low values observed with some amino acids might be explained by the interaction between enzyme and the α-carboxylate group of the amino acid when it is combined with tight binding of its side chain to the enzyme. The interaction between enzyme and α-carboxylate group of some amino acid nucleophiles apparently had an adverse effect on $fa_{max}$ suggesting that alteration of this interaction could have a beneficial effect. Amino acid nucleophiles could occupy a position similar to that of the $P_1'$ amino acid residue of peptide substrates. If this is the case, then the amino acids in CPD-Y involved in the binding of the C-terminal carboxylate group of peptide substrates would also be important for the binding of the α-carboxylate group of amino acid nucleophiles. The binding of the C-terminal carboxylate group of peptide substrates is dependent on hydrogen bonds from the side chain of Asn51 and Glu145, the latter with the carboxylic acid group in its protonated form, and the optimal position of these two side chains is secured by hydrogen bonds from Glu65 and Trp49. However, this is the situation at low pH where the enzyme efficiently binds peptide substrates: at pH 7.5 where the aminolysis reactions were carried out, Glu145 is in its deprotonted negatively charged form which cannot participate in the binding of the α-carboxylate group. In fact, this negative charge may substantially influence the binding mode of the amino acid nucleophile. Hence, the transacylation reactions might be influenced by mutational replacements of Asn51 and Glu145 and possibly also, due to indirect effects, by replacement of Glu65.

CPD-Y mutants with replacements at positions 51, 65 and 145 were investigated for their ability to catalyze transacylation reactions using H-Val-OH and H-Leu-OH as nucleophiles (Table II).

TABLE II

Carboxypeptidase Mutants with
Improved Characteristics of Acylation

| Mutant | H—Val—OH fa$_{max}$ | K$_{N(app)}$ | H—Leu—OH fa$_{max}$ | K$_{N(app)}$ |
|---|---|---|---|---|
| Wild-type | 0.32 ± 0.01 | 13 ± 1 | 0.35 ± 0.01 | 10 ± 0.8 |
| N51A + E145A | 0[a] | n.d. | 0[a] | n.d. |
| N51A | 0.02[a] | n.d. | 0[a] | n.d. |
| N51s | 0.05[a] | n.d. | 0.03[a] | n.d. |
| N51Q | 0.97 ± 0.02 | 61 ± 3 | 0.96 ± 0.01 | 42 ± 1 |
| E145A | 0.48 ± 0.01 | 79 ± 6 | 0.30 ± 0.01 | 40 ± 2 |
| E145Q | 0.68 ± 0.02 | 41 ± 4 | 0.66 ± 0.06 | 29 ± 8 |
| E6SA | 0.91 ± 0.01 | 69 ± 2 | 0.96 ± 0.01 | 42 ± 1 |
| E65Q | 0.91 ± 0.02 | 75 ± 4 | 0.97 ± 0.01 | 56 ± 1 |
| E65A + E145A | >0.8 | >500 | >0.8 | >0.8 |
| E65A +]E145Q | 1.00 ± 0.03 | 240 ± 15 | >0.8 | >0.89 |

All reactions were performed at pH 7.5 as described herein.
The values for K$_{N(app)}$ are in mM.
[a]The low values prevented the demonstration of saturation of the enzyme and consequently they must be regarded as fa$_{sat}$ values.

The complete removal of the hydrogen bond donating capacity of the side chains at positions 51 and 145 by incorporation of Ala at both positions, i.e. N51A+E145A, abolished the capacity of the enzyme to accept amino acids as nucleophiles. The same result was obtained with the single mutant N51A suggesting that Asn51 is important for the binding of amino acid nucleophiles prior to the attack on the acyl-enzyme intermediate. However, with the other single mutant E145A, significant aminolysis was obtained and this is consistent with the notion that Glu145 at pH 7.5 plays a minor role in the binding of amino acid nucleophiles. Nevertheless, with H-Val-OH and H-Leu-OH as nucleophiles, K$_{N(app)}$ was 4–5 times higher using E145A as compared with the wild-type enzyme.

It is common to all the positions 65 and 145 mutants, i.e. E65A, E65Q, E145A, E145Q, E65A+E145A and E65Q+ E145Q, that K$_{N(app)}$ with H-Val-OH and H-Leu-OH increased by a factor of 5 to 10. Simultaneously, an increase in fa$_{max}$ was observed except with E145A. With E65A and E65Q, the fa$_{max}$ values exceeded 0.90 and, as a result, it is possible with these enzymes to obtain much higher yields when hydrophobic amino acids are used as nucleophiles. Although not meant to be a limitation of the invention, Glu65 and Glu145 do not appear to be directly involved in the binding of the α-carboxylate group of amino acid nucleophiles at the pH where the reaction is carried out, they seem to exert an indirect influence such that their replacement affect the binding mode, as indicated by the elevated fa$_{max}$ values. When amino acid amides are used as nucleophiles, the presence of the negatively charged Glu145 does not appear to exert a negative effect since the fa$_{max}$ values consistently are high.

Asn51 was replaced with other amino acid residues and these enzymes were tested. Replacing Asn51 with Ser or Gln affected fa$_{max}$ in different directions. With N51S and H-Val-OH and H-Leu-OH as nucleophiles, fa$_{max}$ was 0.05 and 0.03, respectively (Table II). With N51Q, they were 0.97 and 0.96, respectively, and with the wild-type enzyme, fa$_{max}$ was 0.35 with both nucleophiles.

With FA-Phe-OMe as substrate and H-Val-OH as nucleophile, the same influence of the group at position 51 on fa$_{max}$ was observed (data not shown). The kinetic parameters for the hydrolysis of FA-Phe-Val-OH by these mutants are: k$_{cat}$=1500 min$^{-1}$, K$_M$=0.085 mM, k$_{cat}$/K$_M$=18000 min$^{-1}$ mM$^{-1}$ (N51Q); k$_{cat}$=8100 min$^{-1}$, K$_M$=0.17 mM, k$_{cat}$/K$_M$= 48000 min$^{-1}$ mM$^{-1}$ (N51S) as compared with k$_{cat}$=6500 min$^{-1}$, K$_M$=0.047 mM, k$_{cat}$/K$_M$=140000 min$^{-1}$ mM$^{-1}$ (wild-type). Normally, in serine protease catalyzed peptide bond hydrolysis, the acylation step is rate-limiting. However, this is not the case in CPD-Y catalyzed hydrolysis of FA-Phe-X-OH substrates (X=amino acid residue) since the k$_{cat}$ values show only little dependence on the structure of X. Thus, the rate of the deacylation step exerts an influence on K$_{cat}$. The k$_{cat}$ values for the hydrolysis of FA-Phe-Val-OH increase in the order N51Q<wild-type<N51S and this correlates inversely with fa$_{max}$ values with H-Val-OH as nucleophile which decrease in the order N51Q>wild-type>N51S.

The results in Table II show that, among the mutants tested, the highest fa$_{max}$ values were obtained with N51Q and, as a consequence, this enzyme was deemed the most suitable supplement to the wild-type enzyme as a catalyst in this particular type of peptide synthesis. This was further investigated by determination of the K$_{N(app)}$ and fa$_{max}$ values for a number of different amino acid nucleophiles using 51Q (Table III) and the results may be compared to those obtained with the wild-type enzyme. For H-His-OH and the hydrophobic amino acids, the fa$_{max}$ values were significantly higher with N51Q as compared with the wild-type enzyme. However, with some amino acids, the Asn51→Gln had no or only small effect on fa$_{max}$, i.e., those where fa$_{max}$ with the wild-type enzyme was zero or exceeded 0.9. With all nucleophiles, K$_{N(app)}$ was significantly higher with N51Q as compared with the wild-type enzyme and this had the consequence that fa$_{max}$ with some amino acids could not be reached due to limited solubility of the nucleophile. The value of fa$_{max}$ obtained at the highest possible concentration of nucleophile, i.e. fa$_{sat}$, has been listed in Table III and this value represents the highest possible yield that can be obtained in aqueous solution at pH 7.5. A comparison of the fa$_{sat}$ values obtained with the wild-type enzyme leads to the conclusion that N51Q is superior to the wild-type enzyme with the hydrophobic amino acids as nucleophiles.

TABLE III

N51Q Catalyzed Aminolysis of an Ester Substrate
Using Amino Acids AE Nucleophiles.
The Influence of Amino Acid Structure on the Parameters
for the Aminolysis Reaction Compared to Wild-Type

| | N51Q | | | Wild-Type | | |
|---|---|---|---|---|---|---|
| Nucleophile | fa$_{sat}$ | fa$_{max}$ | K$_{N(app)}$ | fa$_{sat}$ | fa$_{max}$ | K$_{N(app)}$ |
| H—Gly—OH | 0.18 | >0.8 | >20.000 | 0.60 | 0.92 ± 0.01 | 1500 ± 50 |
| H—Ser—OH | 0.66 | 0.87 ± 0.01 | 1100 ± 40 | 0.78 | 0.87 ± 0.01 | 310 ± 20 |

TABLE III-continued

N51Q Catalyzed Aminolysis of an Ester Substrate
Using Amino Acids AE Nucleophiles.
The Influence of Amino Acid Structure on the Parameters
for the Aminolysis Reaction Compared to Wild-Type

|  | N51Q | | | Wild-Type | | |
| --- | --- | --- | --- | --- | --- | --- |
| Nucleophile | $fa_{sat}$ | $fa_{max}$ | $K_{N(app)}$ | $fa_{sat}$ | $fa_{max}$ | $K_{N(app)}$ |
| H—Lys—OH | 0.73 | 0.97 ± 0.06 | 960 ± 140 | 0.79 | 0.81 ± 0.03 | 190 ± 30 |
| H—His—OH | 0.18 | 0.53 ± 0.06 | 520 ± 80 | 0.20 | 0.27 ± 0.01 | 87 ± 9 |
| H—Gln—OH | 0.41 | 1.00 ± 0.03 | 540 ± 30 | 0.64 | 0.90 ± 0.02 | 150 ± 8 |
| H—Glu—OH | 0 | n.d. | n.d. | 0 | n.d. | n.d. |
| H—Ala—OH | 0.84 | 0.99 ± 0.01 | 250 ± 10 | 0.85 | 0.91 ± 0.02 | 83 ± 7 |
| H—Val—OH | 0.87 | 0.97 ± 0.02 | 61 ± 3 | 0.30 | 0.32 ± 0.01 | 13 ± 1 |
| H—Leu—OH | 0.74 | 0.96 ± 0.01 | 42 ± 1 | 0.32 | 0.35 ± 0.01 | 10 ± 1 |
| H—Phe—OH | 0.74 | 0.89 ± 0.03 | 29 ± 1 | 0.14 | 0.15 ± 0.01 | 9.5 ± 1 |
| H—Pro—OH | 0 | n.d. | n.d. | 0 | n.d. | n.d. |

EXAMPLE 3

Alteration of Leaving Group Preference for Mutant Carboxypeptidase Y Catalyzed Transpeptidation Reactions With ester substrates, serine carboxypeptidases exhibit no dependence on the nature of the leaving group. However, with peptide substrates where an amino acid acts as leaving group, this is not always the case. With carboxypeptidase Y, the most commonly employed serine carboxypeptidase, high yield of transpeptidation is only achieved when the leaving group is a hydrophilic amino acid. However, since carboxypeptidase Y in hydrolysis reactions exhibits a preference for hydrophobic amino acid leaving groups ($P_1'$ amino acids), it would be beneficial, due to higher rate and specificity of the reaction, if such leaving groups were permissible in transpeptidation reactions as well. This would also permit modification of peptides and proteins, as isolated from natural sources, which presently are excluded due to hydrophobic C-terminal amino acid residues. The low yields due to the described leaving group dependence has prevented further development of a method for incorporation of labelled amino acid residues into peptides and proteins with the purpose of facilitating amino acid sequence determinations.

Mutants of carboxypeptidase Y were examined for the capacity to enhance yields of transacylation with substrates having leaving groups that are not hydrophilic. Some amino acid substitutions made in the active site of mutant carboxypeptidase Y enzymes were also made knowing they were not likely to improve the yields of transacylation reactions, but rather to investigate the mechanism of action of the leaving group dependence.

Carboxypeptidase Y was obtained from Carlbiotech, Copenhagen, Denmark. All amino acids/amino acid derivatives were purchased from Bachem, Switzerland. The mutations in the structural gene for carboxypeptidase Y were carried out as described in Example I. The mutants N51S, N51Q, E65A, and E145A were isolated as described in Example I and their purity was ascertained by SDS polyacrylamide gel electrophoresis performed on a Pharmacia Phast-system. The substrates FA-Ala-Gln-OH, FA-Ala-Arg-OH, FA-Ala-Lys-OH, Hippuryl-L-Phe-OH, and Hippuryl-L-β-Penyllactic acid were purchased from Bachem, Switzerland. The preparation of the following substrates were carried as previously described: FA-Ala-OBzl, FA-Ala-Ala-OH, FA-Ala-Val-OH, FA-Ala-Leu-OH, and FA-Ala-Phe-OH. Breddam et al., *Carlsberg Res. Comm.*, 49:535 (1984).

Aminolysis reactions were carried out in the following way. The nucleophile was dissolved in 50 mM HEPES, 5 mM EDTA and pH was adjusted to 7.5, 5 μl substrate (8 mM FA-Ala-OBzl or FA-Ala-Xaa-OH in methanol) was added to 190 μl nucleophile solution followed by 5 μl enzyme diluted in buffer to the appropriate concentration, resulting in a substrate concentration of 0.2 mM. During the reaction, 20 μl aliquots were removed from the reaction mixture and added to 50 μl 1% trifluoroacetic acid to quench the reaction. The reactant composition was determined by HPLC using a Waters HPLC equipped with a C-18 Waters Novapac 4μ reverse phase column and various gradients of acetonitrile in 0.1% trifluoroacetic acid. The separation was monitored at 302 nm allowing the direct quantification of the products from the integrated peak areas. The products were collected and identified by amino acid analysis after acid hydrolysis (Pharmacia Alpha Plus analyzer) and by co-chromatography of authentic standards. The fraction of aminolysis (fa) was expressed as the ratio between the formed aminolysis product and the sum of all products being formed, i.e. unconsumed substrate was disregarded in the calculations. The $K_{N,app}$ (a measure for the dissociation constant of the nucleophile) and $fa_{max}$ (the highest possible fa obtained at saturation with nucleophile were determined by fitting the obtained fa values to the equation $fa=fa_{max}/(1+K_{N,app}/N)$.

The enzymatic hydrolysis of FA-Ala-OBzl and the peptide substrates was followed on a Perkin Elmer λ9 spectrophotometer. The substrates were dissolved in methanol at a concentration of 0.5 to 8 mM. A total of 25 μl of substrate solution was added to 955 μl of 50 mM HEPES, 5 mM EDTA, pH 7.5, to give initial substrate concentrations in the cuvette, $s_0$, of 1.25 to 200 μM. The cleavage of the substrate was followed with time by monitoring the decrease in absorbance at 337 nm and from this the initial rates of hydrolysis $v_0$, was determined. For FA-Ala-OBzl, the $k_{cat}/K_M$ value was determined by fitting to the following form of the Michaelis-Menten equation: $v_0=e_0$ $(k_{cat}/K_M)/(1/K_M+1/s_0)$. For the peptide substrates, the $k_{cat}K_M$ values were determined by fitting to the equation $v_0=(k_{cat}/K_M)e_0s_0$, which is valid when $s_0<K_M$. All fits of the parameters $k_{cat}/K_M$, $fa_{max}$ and $K_{N,app}$ were performed using the Grafit program (Leatherbarrow, R. J., Grafit version 3.0, Erithacus Software Ltd., Staines, U.K., 1990).

While not meant to be a limitation of the invention, it is believed that in CPD-Y catalyzed hydrolysis reactions, a substrate acylates the essential serine residue which subsequently is deacylated by water, hence completing the hydrolysis reaction. When an amine nucleophile, e.g., an amino acid or amino acid amide, is added to the reaction mixture, the acyl-enzyme will be partitioned between water and the added amino component, in the latter case forming a new peptide bond (transpeptidation).

The saturation curves can be described by equation (1).

$$fa = \frac{fa_{max}}{1 + \frac{K_{N,app}}{N}} \quad (1)$$

The upper limit of the fa, termed $fa_{max}$, is reached when $N \leq K_{N,app}$. $fa_{max}$ can reach a maximum value of 1. This is, however, rarely obtained in practice. The concentration at which $fa_{max}/2$ is reached, termed $K_{N,app}$, describes the affinity of the nucleophile for the enzyme and the dissociation of the aminolysis product.

Peptide esters may function as substrates and, in this case, reaction with the amine component causes elongation of the peptide. The ratio of the hydrolysis to aminolysis reaction is not influenced by the nature of the alcohol leaving group, but that there is a pronounced effect of the nucleophile on $fa_{max}$. Hence, $fa_{max}$ values ranging from 1.00 with H-Gly-NH$_2$ to 0.15 with H-Phe-OH as nucleophile are observed.

When a peptide functions as substrate, in which case the C-terminal amino acid residue is exchanged with the added amino component, the hydrophobicity of the amino acid leaving group exerts a pronounced influence on the hydrolysis/aminolysis ratio. With H-Val-NH$_2$ or H-Gly-NH$_2$ a nucleophile and FA-Ala-XAA-OH (XAA=H-Arg-OH, H-Lys-OH, H-Gln-OH, H-Ala-OH, H-Val-OH, H-Leu-OH, and H-Phe-OH) as substrates, the observed $fa_{max}$ values reached 1.00, 0.99, 0.93, 0.94, 0.22, 0.16, and 0.056, respectively (see Table IV). The differences in $fa_{max}$ suggests that the rate of dissociation of the amino acid leaving group is comparable to that of hydrolysis of the acyl-enzyme with the leaving group bound. Furthermore, they coincide with the observation that the $fa_{max}$ values obtained with the ester substrate and H-Arg-OH, H-Lys-OH, H-Gln-OH, H-Ala-OH, H-Val-OH, H-Leu-OH, and H-Phe-OH as nucleophiles are 0.87, 0.81, 0.90, 0.91, 0.32, 0.35, and 0.15, respectively, and thus similar to the $fa_{max}$ values obtained when these amino acids act as leaving groups (see Table IV).

TABLE IV

Influence of the Amino Acid Nucleophile/Leaving Group On the $fa_{max}$ Values Obtained with Wild-Type CPD-Y

| H—XA—OH | FA—Ala—OBzl + H—Xaa—OH | FA—Ala—Xaa—OH + H—Val/Gly—NH$_2$ |
|---|---|---|
| H—Gln—OH | 0.90 ± 0.03 | 0.93 ± 0.01[a] |
| H—Lys—OH | 0.81 ± 0.03 | 0.99 ± 0.01[a] |
| H—Arg—OH | 0.87 ± 0.01 | 1.00 ± 0.02[b] |
| H—Ala—OH | 0.91 ± 0.02 | 0.94 ± 0.01[b] |
| H—Val—OH | 0.32 ± 0.01 | 0.22 ± 0.01[b] |
| H—Leu—OH | 0.35 ± 0.01 | 0.16 ± 0.01[b] |
| H—Phe—OH | 0.15 ± 0.01 | 0.06 ± 0.01[b] |

[a]H—Gly—NH$_2$ was used as nucleophile and
[b]H—Val—NH$_2$ was used as nucleophile.
Using FA—A—OBzl as substrate, the observed $fa_{max}$ was 1.0 ± 0.01 with H—Gly—NH$_2$ and 0.98 ± 0.01 with H—Val—NH$_2$.

It has previously been suggested that low yields in aminolysis reactions were due to degradation of the products, a theory based on the fact that any product of an aminolysis reaction will be a substrate for CPD-Y. However, in the reactions studied here with FA-Ala-OBzl as substrate, the $k_{cat}/K_M$ for the hydrolysis of the products, under the conditions used in the aminolysis reactions, are 50–100 fold lower than that of the substrate (data not shown). Consequently, no degradation of the aminolysis products is detected with FA-Ala-OBzl as substrate and FA-Ala-Xaa-OH (Xaa=Ala-OH, Val-OH, Leu-OH, Val-NH$_2$) as product.

In order to be able to alter yields obtainable with a specific amino acid acting as leaving group/nucleophile, it is helpful to know what contributes to low $fa_{max}$ values. While not meant to limit the invention, it is believed that the wide range of results with amino acids as leaving groups indicates that the magnitude of the rate constants which enter the expression for $fa_{max}$ are associated with the nature of the amino acid side-chain. It appears that the more hydrophobic the leaving group, the lower the $fa_{max}$. A significant increase in $fa_{max}$ can be achieved by structural alterations within the binding pocket for the side-chain of the $P_1'$ amino acid residue. Alternatively, modification of the interaction between the α-carboxylate group of the leaving group or nucleophile and the binding site for the C-terminal carboxylate group (Asn51, Glu65 and Glu145) will influence $fa_{max}$. Alterations within this region result in CPD-Y derivatives with changed $fa_{max}$ values in transacylation reactions with FA-Ala-OBzl as substrate and various amino acid nucleophiles.

Aminolysis reactions were carried out with the substrates Hippuryl-L-Phe-OH (peptide bond, the N-terminal of the leaving group is a H$_2$N— group) and Hippuryl-L-β-Phenyllactic acid (ester bond, the N-terminal of the leaving group is a HO— group), using H-Gly-NH$_2$ as nucleophile. These two reactions gave us a possibility to evaluate whether the nature of the Phe side-chain carboxyl-terminal or the amino group determines the low $fa_{max}$ value observed with Phe. The aminolytic parameters with phenylalanine or L-β-Phenyllactic acid, respectively, as the leaving group and H-Gly-NH$_2$ as nucleophile were determined: $fa_{max}$ were found to be 0.33±0.01 and 0.96±0.01, respectively, and $K_{N,app}$ to be 0.63±0.06 and 0.47±0.05, respectively. Thus, these reactions suggest that the nature and positioning of the α-amino group contributes to the low yield obtained with some amino acids.

While not meant to be a limitation of the invention, it appears that the conformation in which an amino acid binds within the $S_1'$ site may facilitate or restrain the access of water to the acyl component covalently attached to the essential serine residue (Ser146) due to the positioning of the amino group of the leaving group/nucleophile. It should, thus, be possible to achieve increased $fa_{max}$ values if the binding mode of a specific amino acid within the $S_1'$ binding site is altered to prevent nucleophilic attack of water on the acyl-enzyme.

The reaction FA-Ala-Xaa OH+H-Val-NH$_2$→FA-Ala-Val-NH$_2$+H-Xaa-OH was studied with these mutants. With the mutant N51Q, the $fa_{max}$ values were 0.98, 0.91, and 0.80 with Xaa=Ala, Val, Leu, respectively. Similar results were obtained in the reaction FA-Ala-OBzl+H-Xaa-OH (Xaa= Ala, Val, Leu, and Phe)→FA-Ala-Xaa-OH+HOBzl (see Table V), where the $fa_{max}$ values with Xaa=Val and Leu are 4–5 fold higher than those obtained with the wild-type enzyme. The observation that N51Q exhibits increased $fa_{max}$ values in transpeptidation reactions is probably due to changes in the binding of amino acids within $S_1'$. The mutation results in increased reaction with amine relative to water. This result would be consistent with a shorter distance between the acyl-enzyme and the α-amino group of the nucleophile/leaving group.

TABLE V

Influence of the Amino Acid Nucleophile on
$Fa_{max}$ and $K_{n,aoo}$ Values Using FA—Ala—OBzl as Substrate
and CPD-Y and Various Mutants

| Enzyme | Nucleophile | $Fa_{max}$ | $K_{n,app}$ (mM) | $K_{n,app}/fa_{max}$ (mM) |
|---|---|---|---|---|
| Wild Type | H—Ala—OH | 0.91 ± 0.02 | 83 ± 7 | 91 |
| | H—Val—OH | 0.32 ± 0.01 | 13 ± 1 | 43 |
| | H—Leu—OH | 0.35 ± 0.01 | 10 ± 1 | 29 |
| | H—Phe—OH | 0.15 ± 0.01 | 10 ± 1 | |
| N51S | H—Ala—OH | 0.56 ± 0.05 | 140 ± 4 | 250 |
| | H—Val—OH | n.d.[b] | n.d.[b] | n.d. |
| | H—Leu—OH | n.d.[b] | n.d.[b] | n.d. |
| | H—Phe—OH | n.d.[b] | n.d.[b] | n.d |
| N51Q | H—Ala—OH | 0.99 ± 0.01 | 250 ± 15 | 250 |
| | H—Val—OH | 0.97 ± 0.02 | 61 ± 2 | 63 |
| | H—Leu—OH | 0.96 ± 0.01 | 42 ± 1 | 44 |
| | H—Phe—OH | 0.89 ± 0.03 | 29 ± 1 | 33 |
| E65A | H—Ala—OH | 0.98 ± 0.02 | 280 ± 20 | 290 |
| | H—Val—OH | 0.91 ± 0.01 | 69 ± 2 | 76 |
| | H—Leu—OH | 0.96 ± 0.01 | 45 ± 2 | 47 |
| | H—Phe—OH | 0.89 ± 0.03 | 31 ± 1 | 35 |
| E145A | H—Ala—OH | n.d.[c] | n.d.[c] | 7100 |
| | H—Val—OH | 0.48 ± 0.01 | 79 ± 6 | 160 |
| | H—Leu—OH | 0.30 ± 0.01 | 40 ± 2 | 130 |
| | H—Phe—OH | 0.31 ± 0.01 | 21 ± 1 | 68 | n.d. Not determined due to:
[b]low fa values in the examed concentration range or
[c]$K_{n,app}$ values much larger than N.

In contrast to this, introduction of a serine at position 51 results in $fa_{max}$ values that are reduced to approximately 50% of the wild-type value (Tables V and VI).

TABLE VI

Influence of the Substrate Leaving Group an
$fa_{max}$ and $K_{n,app}$ Values with H—Val—NH$_2$ as Nucleophile
and CPD-Y and Various Mutants

| Enzyme | Nucleophile | $fa_{max}$ | $K_{n,app}$ (mM) | $K_{n,app}/fa_{max}$ (mM) |
|---|---|---|---|---|
| Wild Type | FA—Ala—OBzl | 0.98 ± 0.01 | 1.7 ± 0.1 | 1.7 |
| | FA—Ala—Ala—OH | 0.94 ± 0.01 | 1.8 ± 0.1 | 1.9 |
| | FA—Ala—Val—OH | 0.22 ± 0.01 | 1.5 ± 0.1 | 6.6 |
| | FA—Ala—Leu—OH | 0.16 ± 0.01 | 1.6 ± 0.1 | 9.9 |
| | FA—Ala—Phe—OH | 0.06 ± 0.01 | 1.1 ± 0.1 | 19.6 |
| N51S | FA—Ala—OBzl | 0.97 ± 0.01 | 1.6 ± 0.1 | 1.7 |
| | FA—Ala—Ala—OH | 0.88 ± 0.01 | 1.9 ± 0.1 | 2.2 |
| | FA—Ala—Val—OH | 0.13 ± 0.01 | 1.8 ± 0.1 | 13.9 |
| | FA—Ala—Leu—OH | n.d.[a] | n.d.[a] | n.d. |
| | FA—Ala—Phe—OH | n.d.[a] | n.d.[a] | n.d. |
| N51Q | FA—Ala—OBzl | 0.96 ± 0.01 | 3.1 ± 0.4 | 2.1 |
| | FA—Ala—Ala—OH | 0.98 ± 0.01 | 3.1 ± 0.1 | 3.2 |
| | FA—Ala—Val—OH | 0.91 ± 0.01 | 2.4 ± 0.1 | 2.6 |
| | FA—Ala—Leu—OH | 0.80 ± 0.01 | 2.4 ± 0.1 | 3.0 |
| | FA—Ala—Phe—OH | 0.77 ± 0.01 | 3.1 ± 0.1 | ?? |
| E65A | FA—Ala—OBzl | 0.97 ± 0.01 | 4.2 ± 0.01 | 4.4 |
| | FA—Ala—Ala—OH | 0.96 ± 0.01 | 5.2 ± 0.5 | 5.5 |
| | FA—Ala—Val—OH | 0.67 ± 0.03 | 5.7 ± 0.3 | 8.5 |
| | FA—Ala—Leu—OH | 0.71 ± 0.01 | 5.2 ± 0.1 | 7.4 |
| | FA—Ala—Phe—OH | 0.66 ± 0.01 | 4.7 ± 0.1 | 7.1 |
| E145A | FA—Ala—OBzl | 0.98 ± 0.01 | 3.4 ± 0.4 | 3.5 |
| | FA—Ala—Ala—OH | n.d.[b] | n.d.[b] | n.d. |
| | FA—Ala—Val—OH | 0.80 ± 0.01 | 4.2 ± 0.2 | 5.2 |
| | FA—Ala—Leu—OH | 0.65 ± 0.01 | 4.1 ± 0.1 | 6.3 |
| | FA—Ala—Phe—OH | 0.49 ± 0.01 | 4.1 ± 0.1 | 8.4 | n.d. Not determined due to:
[a]low fa values in the examined concentration range or
[b]considerable degradation of the product This is consistent with the fact that no products are observed with FA-Ala-OBzl as substrate and valine, leucine or phenylalanine as nucleophile and with alanine $fa_{max}$ was reduced from 0.91 to 0.56 (Table V). Thus, with N51S the decreased $fa_{max}$ values observed with FA-Ala-OBzl are also found with FA-Ala-Xaa-OH as substrate, hence repeating the pattern found with N51Q, i.e., that similar changes in $fa_{max}$ are found with either leaving group. While not meant to be a limitation of the invention, this might be due to the serine in the mutant being shorter than the asparagine and subsequent steric changes in the active site that result in more rapid hydrolysis. The results from the aminolysis reactions are in good agreement with those obtained from steady state kinetics, which suggest N51 interacts with the C-terminal α-carboxylate group of peptide substrates.

The characteristics of the mutant E61A are quite identical to those of N51Q. Hence, it exhibits an increase in $fa_{max}$ in the reaction: FA-Ala-OBzl+H-Xaa-OH (Xaa=Val, Leu and Phe)→FA-Ala-Xaa-OH+HOBzl to approximately 0.9 (see Table V) as well as in the reactions where these amino acids act as leaving groups. In the latter reactions, $fa_{max}$ reaches 0.67, 0.71 and 0.66 with -Val-OH, -Leu-OH and -Phe-OH, respectively. Again, we observe similar changes in $fa_{max}$ with the same amino acid as leaving group/nucleophile, the same pattern as previously was found with the mutants on position N51.

With E145A, $fa_{max}$ was increased from 0.22 to 0.890 with valine as leaving group and from 0.16 to 0.65 with leucine. But with valine as nucleophile, $fa_{max}$ is only increased from 0.35 to 0.48, and with leucine reduced from 0.35 to 0.30. Thus, E145A does not show a similar increase in $fa_{max}$ with the same amino acids as nucleophiles. In this way the characteristics of E145A deviate from those of N51S, N51Q and E65A. The fact that with E145A the $fa_{max}$ values in reactions with FA-Ala-OBzl and FA-Ala-Xaa-OH deviate is consistent with to E145 not being involved in the binding of the carboxyl group of an amino acid nucleophile.

From these mutants it has been demonstrated that it is possible to alter the leaving group preference of CPD-Y, hence increasing its potential use in various transpeptidation reactions.

EXAMPLE 4

Alteration of Nucleophile Specificity By Mutant Carboxypeptidase

The characterization of a series of mutationally altered derivatives of this carboxypeptidase Y (CPD-Y) has delineated the nature of the interaction between the C-terminal carboxylate group of the substrate and the enzyme. While not meant to be a limitation of the invention, it is believed that hydrogen bonds from the side chains of Asn51 and Glu145 appear to be responsible for the binding of the C-terminal carboxylate group of peptide substrates. The peptidase activity of CPD-Y is optimal at acidic pH. CPD-Y also catalyzes the release of amino acid amides from peptide amides but this activity is optimal at basic pH. It is likely that at the basic pH range Asn51 interacts with the carbonyl oxygen of the C-terminal carboxyamide group while Glu145 in its deprotonated (carboxylate) form interacts with the —NH$_2$ group of the substrate. Glu65 is hydrogen bonded to Asn51 and Glu 145 thereby orienting the two side chains involved in C-terminal recognition. When these amino acid residues are exchanged by site directed mutagenesis with amino acid residues without the capacity to function as hydrogen bond donors, the $k_{cat}/K_M$ for the release of amino acids and amino acid amides from the C-terminus of peptides and peptide amides is drastically reduced. However, when other amino acid residues with such a capacity are incorporated at these positions, much more activity is retained.

In a number of cases, higher yields with nucleophiles containing a blocked α-carboxylate group, in particular amino acid amides, would be highly desirable. This problem can be approached by protein engineering. In particular, one could imagine that such changes might improve the synthetic capacity of the enzyme by (a) permitting the use of nucleophiles which are poorly accepted by the wild-type enzyme, (b) securing better binding of nucleophiles, (c) providing higher yields, and (d) reducing the rate of degradation of products. We here report the effects of such mutations on transacylation reactions with amino acid derivatives as nucleophiles. Some amino acid substitutions made in mutant proteases were made knowing that they were not likely to enhance yields of transacylation, but rather to study the mechanism of action of binding and catalysis with nucleophilies containing a blocked α-carboxylate group.

Carboxypeptidase-Y was obtained from Carlbiotech, Copenhagen, Denmark. H-Val-OPr, H-Val-OBu, H-Val-NHCH$_3$ and H-Val-NHC$_2$H$_5$ were from Peptech, Sydney, Australia. All other amino acids and amino acid derivatives were from Bachem, Switzerland. The mutants Asn 51→Gly, Cys and Val in the structural gene for CPD-Y and subsequent expression and purification of the mutants N51G and N51C were carried as described in Example 1. The purity of the enzymes was ascertained by SDS polyacrylamide gel electrophoresis. The preparation of the mutants N51A, N51D, N51T, N51Q, N51S, E145A and E145D has previously been described. The mutations Asn51→Cys, Asn51→Gly and Asn51→Val were constructed. However, N51V was not expressed and, thus, only N51C and N51G were isolated. FA-Ala-OBzl, FA-Phe-Ala-OH and FA-Phe-Leu-OH were synthesized by standard methods.

All enzymatic activities toward FA-substrates were determined spectrophotometrically at 329–337 nm using a Perkin Elmer lambda 7 or lambda 9 spectrophotometer thermostated at 25° C. The hydrolysis was carried out in 0.05 M Mes, 1 mM EDTA, pH 6.5 for peptide substrates and in 0.05 M Hepes, 1 mM EDTA, 2.5% (v/v), pH 7.5 for ester substrates, $k_{cat}$ and $K_m$ values were determined using the Enzfitter program.

Among the previously described CPD-Y derivatives, mutationally altered at positions 51, 65 and/or 145, a number were chosen to be investigated for their applicability in peptide synthesis. For the study of aminolysis reactions, the excellent CPD-Y substrate FA-Ala-OBzl was selected and initially the ability of all the CPD-Y derivatives to hydrolyze this substrate was investigated (data not shown). With most mutants the hydrolysis of FA-Ala-OBzl was only slightly affected by replacement of Asn51. In fact, with a number of mutants, elevated $k_{cat}/K_M$ values were observed. With E65A, N51G and, in particular, E145Q, reduced $k_{cat}/K_M$ were observed, possibly due to the effects of minor conformational changes. However, apart from this result, it appears that the interaction between enzyme and the -OBzl leaving group, in spite of its bulkiness, is not adversely affected by mutational replacements at positions 51, 65 and 145. Thus, provided that these enzymes may bind nucleophiles in a productive mode, they should be able to catalyze aminolysis reactions.

The reactions with the valine amides were investigated. With H-Val-NH$_2$, the fraction undergoing aminolysis reaction increased with increasing concentration of nucleophile until it reached 1.00. The results were analyzed according to a model which assumes that nucleophile binds to the acyl-enzyme intermediate prior to the deacylation reaction. The correlation between fa and the concentrations of nucleophile are consistent with K$_{N(app)}$ and fa$_{max}$ values of 16 mM and 1.00, respectively. Thus, the hydrolysis reaction is completely excluded by high concentrations of nucleophile. With the corresponding free amino acid, H-Val-OH, the values for K$_{N(app)}$ and fa$_{max}$, as determined under identical conditions, were 13 mM and 0.32, respectively. Thus, compared to H-Val-NH$_2$, the binding of the free amino acid is much looser and, when it is bound, the binding mode evidently is much less favorable for the aminolysis reaction. The beneficial effect of blocking the carboxylate group is presumably due to elimination of the adverse effects of charge repulsion.

The contribution of Asn51 and Glu145 to the productive binding of amino acid amide nucleophiles was investigated by determination of K$_{N(app)}$ and fa$_{max}$ with H-Val-NH$_2$ using CPD-Y derivatives mutationally altered at positions 51 and 145 (see Table VII).

TABLE VII

Use of CPD-Y Mutants for Aminolysis of
FA—Ala—OBzl Using H—Val—NH$_2$ and N-alkyl
Derivatives Hereof as Nucleophiles

| Enzyme | | Nucleophiles | |
|---|---|---|---|
| | | H—Val—NH$_2$ | H—Val—NH—CH$_3$ |
| Wild-type | K$_{n(app)}$ | 1.6 ± 0.1 | 290 ± 50 |
| | fa$_{max}$ | 0.97 ± 0.01 | 0.80 ± 0.05 |
| N51G | K$_{n(app)}$ | 12 ± 2 | 360 ± 20 |
| | fa$_{max}$ | 0.89 ± 0.02 | 0.76 ± 0.07 |
| N51A | K$_{n(app)}$ | 34 ± 1 | >1200 |
| | fa$_{max}$ | 1.00 ± 0.01 | >0.8 |
| N51S | K$_{n(app)}$ | 3.9 ± 0.1 | 360 ± 50 |
| | fa$_{max}$ | 1.00 ± 0.01 | 0.79 ± 0.05 |
| N51C | K$_{n(app)}$ | 11 ± 2 | 1200 ± 100 |
| | fa$_{max}$ | 0.95 ± 0.01 | 0.72 ± 0.04 |
| N51D | K$_{n(app)}$ | 11 ± 1 | 510 ± 40 |
| | fa$_{max}$ | 0.95 ± 0.01 | 0.70 35 0.03 |
| N51Q | K$_{n(app)}$ | 1.5 ± 0.1 | |
| | fa$_{max}$ | 0.97 ± 0.01 | |
| N145A | K$_{n(app)}$ | 3.1 ± 0.1 | 140 ± 13 |
| | fa$_{max}$ | 0.98 ± 0.01 | 0.97 ± 0.03 |
| E145Q | K$_{n(app)}$ | 8.4 ± 1.0 | |
| | fa$_{max}$ | 0.08 ± 0.01 | |
| E145D | K$_{n(app)}$ | 2.3 ± 0.1 | 580 ± 30 |
| | fa$_{max}$ | 0.98 ± 0.01 | 0.59 ± 0.02 |
| E65A | K$_{n(app)}$ | 2.9 ± 0.3 | |
| | fa$_{max}$ | 0.96 ± 0.01 | |
| N51A + E145A | K$_{n(app)}$ | 100 ± 7 | 640 ± 40 |
| | fa$_{max}$ | 0.95 ± 0.02 | 0.98 ± 0.03 |
| E65A + E145A | K$_{n(app)}$ | 110 ± 3 | 47 ± 4 |
| | fa$_{max}$ | 0.76 ± 0.01 | 0.33 ± 0.01 |

With N51A and N51G, the K$_{N(app)}$ values were increased 8–20 fold and the fa$_{max}$ values remained high. While not meant to be a limitation of the invention, it is believed these results demonstrate that the capacity of the group to donate a hydrogen bond is not required to properly orient the amino acid amide prior to the nucleophilic attack on the acyl-enzyme intermediate but it is apparently important for the binding of the nucleophile. These results are consistent with Asn51 functioning as hydrogen bond donor with the carbonyl oxygen of the carboxyamide group of the nucleophile as acceptor. Asn51 can be replaced with other hydrogen bond donors without impairing this wild-type enzyme. However, the Asn51→Cys mutation caused a significant increase in K$_{N(app)}$ and this is consistent with hydrogen bonds involving Cys being rather weak. With N51D, the value for K$_{N(app)}$ was also significantly elevated but this result is difficult to interpret since it is possible that Asp51 may interact with —NH$_2$ group of the nucleophile.

With E145A and E65A, the values for K$_{N(app)}$ were only doubled and the fa$_{max}$ value remained unchanged. Thus, compared to Asn51, Glu145 and Glu65 appear to be much less important for the interaction with amino acid amide nucleophiles. However, the possibility existed that the remaining glutamic acid, which is negatively charged at pH 7.5, could function in the binding of amino acid amides. To investigate this, the double mutant E65A-E145A was tested and it was found that $K_{N(app)}$ was drastically increased while $fa_{max}$ was somewhat reduced. Thus, the absence of both glutamic acids is detrimental to the binding of amino acid amides but the presence of one of them is sufficient to secure tight binding. In the wild-type enzyme, Glu145 is negatively charged while Glu65 is uncharged and, accordingly, Glu145 is the one interacting with amino acid amides. The very low $fa_{max}$ and significantly elevated $K_{N(app)}$ obtained with E145Q confirm the significance of Glu145 in the interaction with amino acid amides. Most likely, the C-terminus of peptide amides interact with the enzyme in an analogous way with the negatively charged Glu145 acting as a hydrogen bond acceptor. Since both Glu65 and Glu145 in the single mutants may function in this capacity there apparently may be some latitude concerning the length of the hydrogen bond. This is suggested by the fact that shifting the carboxylate group at position 145 one carbon atom away, i.e. E145D, has very small effects on both parameters. The high $K_{N(app)}$ obtained with the double mutant N51A+E145A and H-Val-$NH_2$ as nucleophile show that the effects of the Asn51→Ala and Glu145→Ala mutations are approximately additive but the $fa_{max}$ remained high.

Valine N-methyl amide (H-Val-NH-$CH_3$) binds much less efficiently to CPD-Y than the unblocked H-Val-$NH_2$. However, the $fa_{max}$ is almost as high (0.80). Substitution of Asn51 for Gly, Ala, Ser, Asp or Gln and Glu145 for Ala, Asp or Gln only affected the values for $fa_{max}$ and $K_{N(app)}$ moderately, suggesting that neither Asn51 nor Glu145 is involved in the interaction with H-Val-NH-$CH_3$. The binding mode of this nucleophile, therefore, remains unclear.

EXAMPLE 5

Altering Substrate Preference of Carboxypeptidase Y by a Novel Strategy of Mutagenesis Selected targets of PRC1 were mutagenized randomly and subsequently screened for mutants expressing carboxypeptidase Y (CPD-Y) with increased activity toward poor $P_1$ substrates. From an alignment of the primary structures of CPD-Y and a wheat carboxypeptidase (CPD-W) (Breddam et al., *Carlsberg Res. Commun.*, 52:55–63; 65–71 and 297–311 (1987)) as well as the crystal structure of CPD-W (Liao et al., *J. Biol. Chem.*, 265:6528–6531 (1990), it was predicted which amino acid residues might constitute the surface of the CPD-Y $S_1$ binding pocket. The corresponding codons of PRC1 were chosen as targets for saturation mutagenesis.

The basic technique of the mutagenesis was in vitro DNA synthesis primed by mutagenic (degenerate) synthetic oligonucleotides using single-stranded phagemid DNA as template, followed by transfection of *Escherichia coli*. To facilitate efficient screening of a large population of mutant transformants, a new and generally applicable mutagenesis strategy was developed which eliminates the wild-type background due to unmutagenized plasmids in the subsequent functional screens. Although several existing procedures are highly efficient with respect to the frequency of mutagenesis, a residual portion of the plasmids produced will still be unmutated. If the mutation frequency is, say, 90% and if $10^5$ transformants are produced, then $10^4$ will be wild type. After transformation of yeast, the wild-type transformants can make it very difficult to select the desired mutants in the subsequent screens. To overcome this problem, combinations of stop codons and restriction sites were introduced at each position in the PRC1 gene that was to be targeted by a degenerate oligonucleotide. The stop codons ensure that the e.g. 10% unmutated plasmids will encode inactive CPD-Y, while the introduced restriction sites allow us to monitor the mutation frequency. The mutagenesis itself is performed according to the protocol of Lewis et al. (*Nucleic Acids Res.*, 18:3439 (1990)) on single-stranded phagemid DNA carrying a frameshift mutated ampicillin resistance gene and the nonsense mutated prc1 gene. Mutant strand synthesis is primed in a single reaction with a number of degenerate oligonucleotides to produce mutations in the PRC1 gene and an oligonucleotide that repairs the ampicillin resistance gene. The resulting DNA is used to transform a mismatch-repair deficient *E. coli* strain to ampicillin resistance. Propagation in ampicillin-containing medium selects for progeny of the mutant strand.

Two prc1 deletion strains of yeast were transformed with the plasmid population. In one strain, CPD-Y enters the vacuole, while in the other strain CPD-Y is missorted, secreted and activated extracellularly due to a vps mutation as described by Nielsen et al., *Appl. Microbiol. Biotech.*, 33:307 (1990).

The vps strain, which requires leucine for growth, was used to search for desired mutants in a single direct screen. The transformed cells were plated on synthetic medium lacking leucine but containing one of various N-blocked-X-Leu-OH dipeptides. Only cells which express a protease that can release the terminal leucine can grown on these plates.

The Vps$^+$ strain was used to screen for desired mutants in two steps. First, transformant colonies were overlaid by agar containing a chromogenic substrate which reveals CPD-Y activity. In the second step, the CPD-Y activity from the positive colonies was estimated towards different substrates in a chromogenic microtiter dish assay.

By this procedure, a total of >$10^5$ independent mutants was produced, some of which exhibit increased activities ($k_{cat}/K_m$) toward certain substrates by a factor of up to 150. A number of these mutant plasmids have been sequenced and the encoded enzymes have been purified and characterized kinetically.

Reagents

CBZ-X-Leu-OH peptides and N-acetyl-L-alanine β-naphthyl ester (AANE) were from Bachem; horseradish peroxidase type I, *Crotalus atrox* L-amino acid oxidase type VI, o-dianisidine and Fast Garnet Red GBC salt were from Sigma. Oligonucleotides were synthesized on an Applied Biosystems 394 DNA-RNA Synthesizer. LB, 2xYT and SOC medium were prepared according to Sambrook et al., *Molecular Cloning. A Laboratory Manual*, Cold Spring Harbor, N.Y. (1989). SC and YPD medium were prepared according to Sherman, *Methods Enzymol.*, 194:3–21 (1991), with slight modifications (Tullin et al., *Yeast*, 7:933–941 (1991)).

Strains

*E. coli* BMH71-18mutS (thi supE Δ(lac-proAB) [mutS::Tn10] F'[proAB$^+$ laqI$^q$ lacZΔM15]) (Kramer et al. *Cell*, 38:879 (1984); Zell et al. *EMBO J.*, 6:1809 (1987)); *E. coli* JM109 (recA1 supE44 endA1 hsdR17 gyrA96 relA1 thi Δ(lac-proAB) F'[traD36 proAB$^+$ laqI$^q$ lacZΔM15]) (Yanisch-Perron et al., *Gene*, 33:103 (1985)); *S. cerevisiae* JHRY20-2CΔ3 (MATa Δprc1 leu2-3 leu2-112 ura3-52 his3-Δ200 prc1-Δ3::HIS3) (Blachly-Dyson et al., *J. Cell Biol.*, 104:1183 (1987)); *S. cerevisiae* W2579 (MATa Δprc1 leu2-3 leu2-112 ura3-52 vpl1-1) (Nielsen et al. (1990) cited supra.). The vpl1 gene has been renamed vps1 (Robinson et al., *Mol. Cell. Biol.,* 8:4936 (1988)). K2579LLR was isolated in the present study as a spontaneous mutant of W2579 that requires less leucine for growth.

Plasmids

The 2.2 kb EcoRI 2μ fragment taken from YEp24 (Botstein et al., *Gene,* 8:17–24 (1979)) was blunted and inserted into the blunted ClaI site of pSELECT (Lewis et al., 1990 cited supra.) in the orientation that places the HINDIII site close to lacZ. The 1.1 kb HindIII URA3 fragment taken from YEp24 was blunted and inserted clockwise into the blunted StyI site of the resulting plasmid to produce pYSEL. The SalI-PvuII fragment of pWI3 (Winther et al., *Eur. J. Biochem.,* 179:681 (1991)) with the PRC1 gene under control of its own promoter was blunted and inserted clockwise into the blunted SalI-BamHI fragment of pYSEL to produce the phagemid shuttle vector pYSP1. A combined stop codon/restriction site was introduced into pYSP1 at each of the four selected targets for mutagenesis of the PRC1 gene (Table VIII). The resulting plasmid, pYSP32, carries ori, tet$^+$, bla$^-$, the fl ssDNA replication origin, a functional fragment of 2μ, URA3 and prc1. Single-stranded DNA produced from this phagemid is complementary to the sequence indicated in Table VIII.

(1988). Transformation of yeast was performed according to Schiestl and Gietz, *Curr. Genet.,* 16:339 (1992).

Preparation of Single-stranded Phagemid DNA

*E. coli* JM109 transformed with pYSP32 was grown to an $OD_{600}$ of 0.5 in 2×YT+50 mg/l tetracycline. One milliliter of this culture was superinfected with 20 μl of a >10$^9$ p.f.u./ml M13K07 helper phage stock in a 500 ml Erlenmeyer bottle. After incubation for 1 hour at 37° C., 200 ml 2×YT+50 mg/l tetracycline +50 mg/l kanamycin was added. After incubation with agitation overnight at 37° C., ssDNA was purified by standard procedures (Sambrook et al., *A Guide to Molecular Cloning* (1989)). Kanamycin selects for cells superinfected with helper phage M13K07.

Mutagenesis

Mutagenesis was performed according to the protocol of Lewis et al. (1990) (cited supra) with slight modifications. Single-stranded pYSP32 (0.2 pmol) was mixed with 0.5 pmol ampicillin-repair oligonucleotide (Promega, Altered Sites Kit) and 2 pmol of each mutagenic degenerate oligonucleotide in 80 μl 2× annealing buffer (20 mM Tris-HCl pH 7.5, 10 mM MgCl$_2$, 50 mM NaCl), heated to 70° C. for 5 minutes and allowed to cool slowly (~1 hour) to room temperature. After the annealing reaction 10 μl 10× synthesis buffer (100 mM Tris-HCl pH 7.5, 5 mM of each of the four dNTPs, 10 mM ATP, 20 mM DTT), 10 Weiss units T4 ligase

TABLE VIII

Nucleotide Sequence of the Wild-type PRC1 Gene
and pYSP32 at the Oligonucleotide Targets Cpy$^+$
Wild type PRC1 and CPY

```
              147                 178                 215 216                 340 341
      ..TCC TAC GCC..     //..GGC CTC ACT..     //..TTG GAA CGT TGT..     //..TTC ATC TGT ACC..(100)
          Tyr                  Leu                  Glu Arg                    Ile Cys
``` prc1 gene of pYSP32

```
           ochre                opal                 amber                   ochre
      ..TAA GCT TCC..     //..TGA ATT CCT..     //..TAG CCC GGG TGT..     //..TAA ATC GAT ACC.. (0)
          HindIII             EcoRI                   SmaI                    ClaI
```

Combination of mutagenic oligonucleotides

Series 1:  ..TCC TAC GCC.. + ..GGC CTC ACT.. + ..TTG GAA CGT TGT.. + ..TTC ATC TGT ACC..        50

Series 2:  ..TCC NNN GCC.. + ..GGC NNN ACT.. + ..TTG NNN NNN TGT.. + ..TTC NNN NNN ACC..         0

Series 3:  ..TCC TAC GCC.. + ..GGC NNN ACT.. + ..TTG NNN NNN TGT.. + ..TTC NNN NNN ACC..        10

Series 4:  ..TCC TAC GCC.. + ..GGC NNN ACT.. + ..TTG GAA CGT TGT.. + ..TTC NNN NNN ACC..         0.4

Series 5:  ..TCC TAC GCC.. + ..GGC CTC ACT.. + ..TTG NNN NNN TGT.. + ..TTC NNN NNN ACC..         1

Series 6:  ..TCC TAC GCC.. + ..GGC NNN ACT.. + ..TTG GAA CGT TGT.. + ..TTC ATC TGT ACC..        10

Series 7:  ..TCC TAC GCC.. + ..GGC CTC ACT.. + ..TTG NNN NNN TGT.. + ..TTC ATC TGT ACC..        50

Series 8:  ..TCC TAC GCC.. + ..GGC CTC ACT.. + ..TTG GAA CGT TGT.. + ..TTC NNN NNN ACC..         0.7

N indicates that an equal mixture of all four nucleotides was used during oligonucleotide synthesis at the indicated position. All mutagenic oligonucleotides were 33 bases long and the degenerate based were situated at the center. The right column indicates the fraction of yeast transformants from each type of DAN the express CPD-Y with detectable activity in the color overlay assay.

Transformation

Transformation of *E. coli* was performed with a Bio-Rad Gene Pulser set at 25 μF, 200 Ω and 2.5 kV in 2 mm cuvettes according to Dower et al., *Nucleic Acid Res.,* 16:6127 (New England Biolabs), 20 units T4 DNA polymerase (Promega) and H$_2$O to 100 μl were added. The polymerase/ligation reaction was incubated at 37° C. for 2 hours. Subsequently the reaction mixture was phenol extracted, ethanol precipitated, resuspended and used to transform electro-competent *E. coli* BMH71-18mutS cells. After incubating the transformed cells for 45 min at 37° C. in SOC, an aliquot was plated on LB plates with 60 mg/l ampicillin to determine the number of transformants, while the rest of the cells were grown overnight in 50 ml LB with 60 mg/l ampicillin. A plasmid preparation from this primary culture will contain up to about 50% ampicillin sensitive plasmids originating from the unmutated parent strand. To enrich for the mutants, 1 µg miniprep DNA from this culture was used for a secondary transformation of JM109. One microgram of miniprep DNA from the JM 109 transformant culture was used to transform the yeast strains K2579LLR and JHRY20-2CΔ3.

Sequencing

DNA sequencing was performed by the Applied Biosystems dsDNA Taq DyeDeoxy™ terminator procedure for use with the Applied Biosystems Model 373A DNA sequencing system.

Plate Activity Screen

Yeast strain K2579LLR was transformed with the mutated population of pYSP32 and plated on SC-ura-leu supplemented with 1.5 mM of a poor CBZ-X-Leu-OH peptide substrate as an enzyme-dependent leucine source. $P_1$ of the substrate was either Glu, Gly, Ser, His, Pro, Trp or Lys. The cells can grow on this medium only if they express proteases capable of releasing the C-terminal leucine. However, CPD-Y is not the only protease secreted by the cells that can catalyze this cleavage. Thus, a minimum level of CPD-Y activity is necessary not only to release sufficient leucine for growth, but also in order to discriminate CPD-Y dependent growth from the background growth. Based on experiments with characterized CPD-Y mutants, it is estimated that the $k_{cat}/K_n$ must be above ~10,000–25,000 $min^{-1}mM^{-1}$, dependent on the substrate.

Color Overlay Screen

Yeast strain JHRY20-2CA3 was transformed with the mutated population of pYSP32 and plated on SC-ura plates, which were incubated at 30° C. until colonies reached a diameter of 2–3 mm. Then each plate was overlaid with a fresh mixture of 3 ml 0.6% agar in water at 50° C. and 2 ml dimethylformamide containing 0.25% AANE at room temperature. After incubation for 5 min at room temperature, 5 ml 0.4% Fast Garnet Red GBC salt in 10 mM sodium phosphate pH 7.0 buffer was poured on top; after 5 min incubation the plates were then rinsed in tap water. Colonies expressing active CPD-Y appear red, while those lacking vacuolar CPD-Y activity appear white (modified from Jones, 1977). Colonies expressing active CPD-Y were isolated by streaking onto SC-ura plates.

Coupled Assay Screen

After incubation for 3–4 days on SC-ura plates of JHRY20-2CΔ3 transformants expressing active mutant CPD-Y, ~1 mm³ of cells was picked with a toothpick and suspended in 200 µl water. After aliquoting 20 µl cell suspension into each of eight microtiter wells, 100 µl substrate mixture (50 mM MES pH 6.5, 1 mM MnCl₂, 50 µg/ml peroxidase, 100 µg/ml L-amino acid oxidase, 100 µg/ml o-dianisidine and 1 mM CBZ-X-Leu-OH) were added. $P_1$ of the substrate (X) was either Phe, Glu, Gly, Ser, His, Pro, Trp or Lys. The plates were incubated at room temperature, and $OD_{560}$ was measured at times 0, 1 and 16 hour on a Perkin Elmer Lambda Microplate Reader (modified from Lewis and Harris, 1967, cited supra).

The activity of each mutant was normalized to that of the wide type as follows. First, all absorption values were corrected by subtracting the background (absorption at same time point in wells without cells). The difference in correction absorption between two time points (corresponding to the amount of hydrolysis) was then normalized to account for variations in cell number, by dividing by the OD of the cells (OD of well with cells at time point 0 minus OD of well without cells at time point 0). Finally, the obtained activity estimate was divided by the corresponding estimate for the wild type. Time point 0 and 1 hour were used to calculate the relative activity towards CBZ-Phe-Leu-OH, while time points 0 and 16 hour were used to calculate the relative activity towards all other substrates.

Isolation and Kinetic Characterization of Mutant Forms of CPD-Y

Over-expression of selected mutant enzymes was performed according to Nielsen et al. (1990) cited supra. The mutant BamHI-BamHI PRC1 fragments of pYSP32 were inserted into the GAL expression vector pRA21 and introduced into yeast strain K2579LLR. The plasmid pRA21 is derived from p72UG (Nielsen et al. (1990) cited supra) by replacing the 918 bp BglII-SalI fragment with the 638 bp BglII-PvuII fragment of pWI3, thereby deleting the BamHI site downstream of the PRC1 gene. Mutant forms of CPD-Y were purified from culture supernatants by affinity chromatography as described in Example 1. Kinetic parameters were determined by measuring rates of hydrolysis at 25° C. of CBZ-X-Leu-OH substrates spectrophotometrically at 224 nm in 10 mM sodium phosphate buffer pH 6.5. The concentrations of substrates ranged from 0.01 to 0.5 mM. Accurate measurements were not possible with substrate concentrations exceeding 0.5 mM due to the high absorption of the substrate.

By studying the crystal structure of the wheat carboxypeptidase CPD-W (Liao et al (1990) cited supra), the amino acid positions Pro60, Tyr156, Leu187, Phe224, Ile225, Val334 and Val335 were found to constitute the bottom, end and sides of the $S_1$ binding pocket of carboxypeptidase W. These positions of CPD-W correspond to amino acid positions Pro54, Tyr147, Leu178, Glu215, Arg216, Ile340 and Cys341 of CPD-Y according to an alignment of the primary structures of the two enzymes (Breddam et al. (1987) cited supra; Sorensen et al., *Carlsberg Res. Commun.*, 52:285 (1987)). We hypothesized that these amino acid residues constitute the $S_1$ binding pocket of CPD-Y. As Pro60 contributes very little to the surface of $S_1$ of CPD-W, Pro54 of CPD-Y was not included in any of the mutagenesis experiments, and as Tyr156 is next to the active Ser155 of CPD-W and its contribution to the surface of $S_1$ is also minor, Tyr147 of CPD-Y was only included in one mutagenesis experiment.

The crystal structure of yeast carboxypeptidase Y (Endrizzi et al., *Biochemistry*, 33:11106 (1994)) confirms that this model is correct in many of its features. The model correctly predicts 4 of 9 residues in the $S_1$ binding site. Pro54 of carboxypeptidase Y is predicted to be at most a marginal part of the $S_1$ binding site; it is in fact absent from the $S_1$ site. The model that used the crystal structure of wheat carboxypeptidase-W and the sequence of yeast carboxypeptidase Y yielded accurate guidance for construction of mutants of carboxypeptidase Y.

Eight different series of mutagenesis of pYSP32 were carried out, randomly mutating various numbers of codons, from 1 to 6, simultaneously (Table VIII): series 1, all codons reverted to wild type; series 2, positions 147, 178, 215, 216, 340 and 341 degenerated; series 3, positions 178, 215 and 216 degenerated; series 4, positions 178, 340 and 341 degenerated; series 5, positions 215, 216, 340 and 341 degenerated; series 6, position 178 degenerated; and series 8, positions 340 and 341 degenerated. In all series, all mutant codons present in pYSP32 that we not subjected to random mutagenesis were reverted to wild type (Table VIII). All degenerate mutagenic oligonucleotides were designed relatively long (33 bases) to minimize biased annealing of oligonucleotides complementary to the introduced stop codons and restriction sites.

A sensitive two-step screening strategy was employed. First, to differentiate transformants expressing active CPD-Y, we have used a modification of the overlay procedure of Jones (1977) for staining CPD-Y containing yeast colonies. Instead of using APNE (N-acetyl-DL-phenylalanine β-naphthyl ester) as a CPD-Y substrate, we have used AANE, since we find that the background staining of inactive CPD-Y transformants is much lower with AANE, thus making it possible to identify transformants with low CPD-Y activity. Furthermore, it was anticipated that most active CPD-Y $S_1$ mutants would accommodate the smaller $P_1$ side chain of AANE better than the larger side chain of APNE.

Colonies of yeast strain JHRY20-2CΔ3 transformed with DNA from all mutagenesis series were screened by this assay. In the wild type control mutagenesis, series 1, half of the transformant colonies express active CPD-Y (Table VIII). If the mutagenesis event at each oligonucleotide target is independent of that of the other three targets, this number corresponds to a mutation frequency of 84% at each target. Of $10^5$ tested transformants from mutagenesis series 2, none had detectable CPD-Y activity. In this series, six codons were mutated simultaneously. Fewer codons were mutated in series 3–6 and 8, which yielded between 0.4 and 10% positive transformants, expressing a wide range of CDP-Y activities as indicated by the color intensities in the overlay assay. Mutagenesis series 7 yielded 50% transformants expressing active CPD-Y and the level of activity of all transformants was indistinguishable from that of the wild type transformants, suggesting that positions 215 and 216 can be varied with little effect on activity towards AANE.

In the second step, we estimated the CPD-Y activity of positive mutants toward eight N-blocked dipeptides (listed in Table IX), by a modification of a chromogenic microtiter dish assay, involving L-amino acid oxidase, peroxidase and o-dianisidine, previously used to monitor carboxypeptidase S activity (Lewis and Harris, 1967; Wolf and Weiser, 1977).

TABLE IX

Estimated CPD-Y Activities of Selected Mutants, Relative to Wild Type Transformants, Towards an Initial Concentration of 1 mM of Eight CBZ—X—Leu—OH Substrates

| | $P_1$ side chain of substrate | | | | | | | |
|---|---|---|---|---|---|---|---|---|
| | Phe | Glu | Gly | Ser | Pro | Trp | His | Lys |
| Wide-type CPD-Y Mutations: | 1 | 1 | 1 | 1 | 1 | 1 | 1 | 1 |
| 178Ser | 0.7 | 1.3 | 1.1 | 0.6 | 1.8 | 1.2 | 1.1 | 9.2 |
| 178Cys | 1.5 | 1.1 | 0.9 | 0.5 | 0.3 | 1.0 | 1.7 | 6.9 |
| 178Cys/215Thr/ 216Trp | 1.0 | 1.1 | 0.8 | 0.4 | 1.6 | 0.9 | 1.1 | 5.3 |

TABLE IX-continued

Estimated CPD-Y Activities of Selected Mutants, Relative to Wild Type Transformants, Towards an Initial Concentration of 1 mM of Eight CBZ—X—Leu—OH Substrates

| | $P_1$ side chain of substrate | | | | | | | |
|---|---|---|---|---|---|---|---|---|
| | Phe | Glu | Gly | Ser | Pro | Trp | His | Lys |
| 178His/215Pro/ 216Thr | 0.9 | 1.0 | 0.8 | 1.1 | 1.2 | 1.5 | 1.1 | 3.6 |
| 178Ala/215Ser/ 216Arg | 1.2 | 1.4 | 1.1 | 1.3 | 0.6 | 1.1 | 1.0 | 4.0 |
| 178Ser/215Ala/ 216Pro | 1.5 | 2.0 | 0.6 | 0.7 | 2.8 | 1.9 | 0.9 | 8.0 |
| 178His/215Thr/ 216Phe | 0.9 | 1.2 | 0.8 | 1.0 | 1.2 | 1.7 | 1.1 | 3.1 |
| 178Asn/215Ala/ 216Gly | 2.8 | 2.0 | 0.7 | 0.7 | 0.9 | 2.0 | 1.3 | 4.4 |
| 178Gly/340Ile/ 341Cys | 0.8 | 0.8 | 0.3 | 0.3 | 0.5 | 0.5 | 0.8 | 4.6 |

Relative activities >2.0 are emphasized in bold print

Transformants of yeast JHRY20-2CΔ3 expressing active CPD-Y from mutagenesis series 3–8 were tested in this assay using an initial substrate concentration of 1 mM. Compared with the wild type, transformants from mutagenesis series 7 all exhibited activity levels around 100% towards all eight tested CBZ-X-Leu-OH substrates. Neither very low nor very high activity levels were observed, suggesting that positions 215 and 216 have little influence on $P_1$ preference. Transformants from mutagenesis series 4, 5 and 8 generally exhibited low and varied activity levels. Most of these exhibited between 10 and 100% CPD-Y activity and none exhibited >200% activity. We conclude that Ile340 and/or Cys341 are important for $K_m$, $k_{cat}$ or production of the enzyme. Transformants from mutagenesis series 3 and 6 showed a broad range of activities with an average around 100%. Several mutants were fund with very low activity levels, just as several were found with very high activity levels towards one of the substrates, CBZ-Lys-Leu-OH. In one case the activity was 9 times the activity of the wild type. To determine which amino acids had been substituted in a number of the most interesting mutants, plasmid DNA was recovered and sequenced (Table IX). The mutant exhibiting the highest increase in activity towards CBZ-Lys-Leu-OH was found to have Leu178 substituted with Ser.

To determine the kinetic parameters of the mutants exhibiting the highest increase in activity, CPD-Y was purified from the mutants 178Ser and 178Ser/215Ala/216Pro by affinity chromatography and analyzed kinetically (Table X).

TABLE X

Kinetic Parameters of Two Selected Mutant CPD-Y Forms Compared with the Wild-type

| Substrate | CPD-Y | $k_{cat}$ (mM/min/mM) | $K_m$ (mM) | $K_{cat}/K_m$ (min$^{-1}$mM$^{-1}$) |
|---|---|---|---|---|
| CBZ—Phe—Leu—OH | Wild-type | 13600 | 0.036 | 380,000 |
| | 178S | 12000 | 0.060 | 200,000 |
| | 178S/215A/216P | 5800 | 0.053 | 110,000 |
| CBZ—Lys—Leu—OH | Wild-type | nd | nd | 24 |
| | 178S | nd | nd | 3,700 |
| | 178S/215A/216P | nd | nd | 2,200 |
| CBZ—Ser—Leu—OH | Wild-type | 800 | 0.070 | 12,000 |
| | 178S | 420 | 0.070 | 6,000 |
| | 178S/215A/216P | 240 | 0.080 | 3,000 |
| CBZ—Ala—Leu—OH | Wild-type | ~25000 | ~0.7 | 36,000 |
| | 178S | nd | nd | 4,800 |
| | 178S/215A/216P | nd | nd | 2,400 |
| CBZ—Glu—Leu—OH | Wild-type | nd | nd | 440 |
| | 178S | nd | nd | 720 |
| | 178S/215A/216P | nd | nd | 500 | nd: Values could not be determined as $K_m$ is >0.5 mM.

The $k_{cat}/k_m$ values of these enzymes towards CBZ-Lys-Leu-OH are 3700 and 2200 min$^{-1}$mm$^{-1}$ respectively, corresponding to a 155- and 199-fold increase relative to the wild type value of 24 min$^{-1}$mM$^{-1}$. These results confirm the importance of the 178Ser mutation and the smaller effect of changes in the side chains at positions 215 and 216.

By introducing stop codons at all targets for random mutagenesis, the wild type background normally present due to unmutagenized plasmids was eliminated, and the wild type PRC1 gene can now only occur by rare mutational reversion. The frequency of such revertants will depend on the mutagenesis efficiency, on how many codons are mutagenized simultaneously and on the number of codons synonymous to the mutagenized codons. With an overall mutagenesis efficiency of 50%, theoretical reversion frequencies of $6\times10^{-9}$, $1\times10^{-4}$, $7\times10^{-5}$, $2\times10^{-6}$, $5\times10^{-2}$, $1\times10^{-3}$ and $7\times10^{-10}$ would be expected for mutagenesis series 1–8 respectively. These low frequencies of wild types enabled selection for rare mutants with increased activity. Without the elimination of the wild type background, it would have been difficult to select the desired mutants from a pool of perhaps 0.5% active mutants and 50% unmutagenized wild type transformants. By this strategy the binding site of any enzyme that has a functional screen can be dissected, amino acid by amino acid, to determine which positions are productive mutagenesis targets. Furthermore, the introduction of a rare restriction site at the oligonucleotide target prior to the mutagenesis simplifies the task of confirming the mutation and reduces sequencing to a minimum.

The results suggest that Leu178, Ile340 and Cys341 contribute to $P_1$ specificity, conceivably by forming part of the surface of the $S_1$ binding pocket. All CPD-Y mutants with increased activity towards Lys in $P_1$ were found to have mutations at position 178. Surprisingly, substituting Leu178 by Ser, Cys, Ala, Gly, Asn or His, all give the same general effect—more activity towards substrates with Lys in $P_1$ (Table X). An explanation for the increased activity towards Lys in $P_1$ of CPD-Y-178 mutants might be that the introduced mutation causes a conformational change of whichever residues constitute the end of $S_1$ in CPD-Y, corresponding to 224 and 225 of CPD-W.

CPD-Y can catalyze the transpeptidation of proline insulin (INS-Pro-Lys-Ala-OH) to produce human insulin amide (INS-Pro-Lys-Thr-NH$_2$), and it has previously been shown that the Cys341 Hg$^{2+}$ modified enzyme, which has 15 times more activity towards Lys in $P_1$, produces 26% human insulin amide product in a transpeptidation reaction (Breddam et al. 1984), whereas the wild type enzyme only produced 4.2%. Thus, the 178Ser mutant, with its 155-fold increase in activity toward Lys in $P_1$, might give even higher yields in such a transpeptidation reaction.

Mutants selected for the ability to hydrolyze a poor CBZ-X-Leu-OH peptide substrate as described herein can also be screened for the ability to transacylate preselected polypeptide substrates and nucleophiles as described in Examples 2 and 3.

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

What is claimed is:

1. A customized carboxypeptidase derived from carboxypeptidase Y, the customized carboxypeptidase having a modified $S_1$ subsite comprising substitution, addition, or deletion of at least one amino acid at a position in the amino acid sequence of carboxypeptidase-Y corresponding to at least one of Tyr 185, Tyr 188, Asn 241, Leu 245 and Trp 312, the customized carboxypeptidase capable of more effectively catalyzing transacylation of a preselected peptide substrate with a preselected nucleophile as compared with the carboxypeptidase Y.

2. The customized carboxypeptidase of claim 1, wherein the modified $S_1$ subsite comprises substitution of at least one of Tyr 185, Tyr 188, Asn 241, Leu 245 and Trp 312.

3. The customized carboxypeptidase of claim 1, wherein the modified $S_1$ subsite comprises deletion of at least one of Tyr 185, Tyr 188, Asn 241, Leu 245 and Trp 312.

4. The customized carboxypeptidase of claim 1, further comprising a modified $S_1'$ subsite including substitution, addition or deletion of at least one amino acid residue.

5. The customized carboxypeptidase of claim 1, further comprising a modified $S_1'$ subsite including substitution of at least one amino acid residue.

6. The customized carboxypeptidase of claim 1, further comprising a modified $S_1'$ subsite including deletion of at least one amino acid residue.

7. The customized carboxypeptidase of claim 1, wherein the modified $S_1$ subsite further comprises substitution at Leu 178.

8. The customized carboxypeptidase of claim 7, wherein the $S_1$ subsite comprises a serine at position 178 (L178S).

9. The customized carboxypeptidase of claim 1, having a modified $S_1$ subsite comprising substitution of at least one of Asn 241, Leu 245, and Trp 312.

10. The customized carboxypeptidase of claim 9 wherein the modified $S_1$ subsite further comprises a substitution at Leu 178.

11. The customized carboxypeptidase of claim 9, wherein the modified $S_1$ subsite comprises a substitution at Asn 241.

12. The customized carboxypeptidase of claim 9, wherein the modified $S_1$ subsite comprises a substitution at Leu 245.

13. The customized carboxypeptidase of claim 9, further comprising a modified $S_1'$ subsite including a substitution at Met 398.

14. The customized carboxypeptidase of claim 1, wherein the transacylation is substantially enhanced as compared with transacylation by the unmodified carboxypeptidase-Y.

15. The customized carboxypeptidase of claim 1, wherein the transacylation is not substantially catalyzed by the unmodified carboxypeptidase-Y.

16. The customized carboxypeptidase of claim 1, wherein the preselected substrate comprises GRF (1–43)-Ala SEQ ID NO: 2 and the preselected nucleophile comprises leucine amide.

17. A process for modifying a preselected peptide substrate by transacylation using a customized carboxypeptidase derived from carboxypeptidase Y, comprising:

(a) forming a mixture of a customized carboxypeptidase, a preselected peptide substrate and a preselected nucleophile, wherein the customized carboxypeptidase having a modified $S_1$ subsite comprises substitution, addition, or deletion of at least one amino acid at a position in the amino acid sequence of carboxypeptidase-Y corresponding to at least one of Tyr 185, Tyr 188, Asn 241, Leu 245, and Trp 312; and the customized carboxypeptidase is capable of more effectively catalyzing transacylation of a preselected peptide substrate with a preselected nucleophile as compared with carboxypeptidase Y; and (b) incubating the mixture sufficiently to form a preselected transacylation product.

18. The process of claim 17, wherein the modified $S_1$ subsite comprises substitution of at least one of Tyr 185, Tyr 188, Asn 241, Leu 245 and Trp 312.

19. The process of claim 17, wherein the modified $S_1$ subsite comprises deletion of at least one of Tyr 185, Tyr 188, Asn 241, Leu 245 and Trp 312.

20. The process of claim 17, further comprising a modified $S_1$ subsite including substitution of at least one amino acid residue.

21. The process of claim 17, further comprising a modified $S_1'$ subsite including deletion of at least one amino acid residue.

22. The process of claim 17, wherein the modified $S_1$ subsite further comprises a serine at position 178 (L178S).

23. The process of claim 17, wherein the customized carboxypeptidase further comprises:

(a) a modified $S_1$ subsite comprising substitution of Leu 178; and (b) a modified $S_1'$ subsite comprising substitution of Met 398.

24. The process of claim 23, wherein the customized carboxypeptidase comprises a modified $S_1$ subsite comprising substitution of at least one of Asn 241 and Lou 245.

25. The process of claim 17, wherein the customized carboxypeptidase further comprises a modified $S_1'$ subsite including substitution of at least one of Asn 51, Thr 60, Phe 64, Glu 65, Glu 145, Leu 272, Scr 297 and Met 398.

26. The process of claim 17, wherein the customized carboxypeptidase further comprises a modified $S_1'$ subsite including substitution of at least one of Gly 52, Cys 56, Tyr 256, Tyr 269 and Cys 298.

27. The process of claim 17, wherein the preselected nucleophile is a single or multiple amino acid unit.

28. The process of claim 17, wherein the preselected nucleophile is selected from the group consisting of an acidic amino acid amide, a basic amino acid amide, a peptide amide, an amino acid, and an amino acid ester.

29. The process of claim 17, wherein the preselected substrate comprises a basic or acidic penultimate amino acid.

30. The process of claim 17, wherein the preselected substrate comprises an arginine at the penultimate position.

31. The process of claim 17, wherein the preselected substrate comprises an acidic or basic amino acid at the penultimate position and the preselected nucleophile comprises an amino acid amide.

32. The process of claim 17, wherein the preselected substrate comprises GRF (1–43)-Ala SEQ ID NO: 2 and the preselected nucleophile comprises leucine amide.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 36 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(vii) IMMEDIATE SOURCE:
       (B) CLONE: GLP-1 (glucagon-like peptide-1)

(xi) SEQUENCE DESCRIPTION: SEQ ID NO:1:

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35

(2) INFORMATION FOR SEQ ID NO:2:

(i) SEQUENCE CHARACTERISTICS:
       (A) LENGTH: 44 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(vii) IMMEDIATE SOURCE:
       (B) CLONE: GRF (1-43)-Ala (Growth hormone releasing factor)

(xi) SEQUENCE DESCRIPTION: SEQ ID NO:2:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Ala
        35                  40

(2) INFORMATION FOR SEQ ID NO:3:

(i) SEQUENCE CHARACTERISTICS:
       (A) LENGTH: 24 amino acids
       (B) TYPE: amino acid
       (C) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(vii) IMMEDIATE SOURCE:
             (B) CLONE: GRF (1-24) (Growth hormone releasing factor)

(xi) SEQUENCE DESCRIPTION: SEQ ID NO:3:

Tyr Ala Asp Ala Ile Phe Thr Asn Ser Tyr Arg Lys Val Leu Gly Gln
 1               5                  10                  15

Leu Ser Ala Arg Lys Leu Leu Gln
            20

(2) INFORMATION FOR SEQ ID NO:4:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo N51Q (xi) SEQUENCE DESCRIPTION: SEQ ID NO:4:

GGATCCGGTC ATCCTTTGGT TGCAAGGGGG T                                    31

(2) INFORMATION FOR SEQ ID NO:5:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

TAAGCTTCC                                                              9

(2) INFORMATION FOR SEQ ID NO:6:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TGAATTCCT                                                                            9

(2) INFORMATION FOR SEQ ID NO:7:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

TAGCCCGGGT GT                                                                       12

(2) INFORMATION FOR SEQ ID NO:8:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

TAAATCGATA CC                                                                       12

(2) INFORMATION FOR SEQ ID NO:9:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

-continued (xi) SEQUENCE DESCRIPTION: SEQ ID NO:9:

TCCTACGCC                                                                                      9

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

TTGGAACGTT GT                                                                                 12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

TTCATCTGTA CC                                                                                 12

(2) INFORMATION FOR SEQ ID NO:12:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

GGCCTCACT                                                                                      9

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
            (B) CLONE: Olio wt11

(xi) SEQUENCE DESCRIPTION: SEQ ID NO:13:

GTTTCTGTCC TTGTGAGACA AAATTTCAGA                                              30

(2) INFORMATION FOR SEQ ID NO:14:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
            (B) CLONE: Olio W49F (xi) SEQUENCE DESCRIPTION: SEQ ID NO:14:

GGATCCGGTC ATCCTTTTCT TGAACGGG                                                28

(2) INFORMATION FOR SEQ ID NO:15:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
            (B) CLONE: Olio N51A (xi) SEQUENCE DESCRIPTION: SEQ ID NO:15:

GCAAAGGATC CGGTCATCCT TTGGTTGGCA GGGGGCCA                                     38

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear

```
        (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
              (B) CLONE: Oligo pUC19 spl (xi) SEQUENCE DESCRIPTION: SEQ ID NO:16:

GCAAGGCGAT TAAGTTGGGT                                                 20

(2) INFORMATION FOR SEQ ID NO:17:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
              (B) CLONE: Oligo E145A (xi) SEQUENCE DESCRIPTION: SEQ ID NO:17:

GGCGTAGGAA GCCCCAGCGA T                                               21

(2) INFORMATION FOR SEQ ID NO:18:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
              (B) CLONE: Oligo E65A and oligo wt1

(xi) SEQUENCE DESCRIPTION: SEQ ID NO:18:

CTGTTCTTTG CATTAGGACC C                                               21

(2) INFORMATION FOR SEQ ID NO:19:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (ii) MOLECULE TYPE: Genomic DNA
```

-continued

```
       (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo N51E (xi) SEQUENCE DESCRIPTION: SEQ ID NO:19:

GCAAAGGATC CGGTCATCCT TTGGTTGGAC GGGGGCCA                              38

(2) INFORMATION FOR SEQ ID NO:20:

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo N51Q (xi) SEQUENCE DESCRIPTION: SEQ ID NO:20:

GGATCCGGTC ATCCTTTGGT TGGAAGGGGG CCA                                   33

(2) INFORMATION FOR SEQ ID NO:21:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo N51Q (xi) SEQUENCE DESCRIPTION: SEQ ID NO:21:

GGATCCGGTC ATCCTTTGGT TGCAGGGGGT                                       30

(2) INFORMATION FOR SEQ ID NO:22:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO
```

(iv) ANTI-SENSE: NO (v) FRAGMENT TYPE:

(vi) ORIGINAL SOURCE:

(vii) IMMEDIATE SOURCE:
             (B) CLONE: Oligo N51Q (xi) SEQUENCE DESCRIPTION: SEQ ID NO:22:

GGATCCGGTC ATCCTTTGGT TGAGTGGGGG T                                                31

(2) INFORMATION FOR SEQ ID NO:23:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo N51T (xi) SEQUENCE DESCRIPTION: SEQ ID NO:23:

GGATCCGGTC ATCCTTTGGT TGACTGGGGG T                                                31

(2) INFORMATION FOR SEQ ID NO:24:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo E145D (xi) SEQUENCE DESCRIPTION: SEQ ID NO:24:

GGCGTAGGAA TCCCCAGCGA T                                                          21

(2) INFORMATION FOR SEQ ID NO:25:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:25:

GGCGTAGGAA TTCCCAGCGA T            21

(2) INFORMATION FOR SEQ ID NO:26:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo E145Q (xi) SEQUENCE DESCRIPTION: SEQ ID NO:26:

GGCGTAGGAT TGCCCAGCGA T            21

(2) INFORMATION FOR SEQ ID NO:27:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(vii) IMMEDIATE SOURCE:
             (B) CLONE: Oligo E145S (xi) SEQUENCE DESCRIPTION: SEQ ID NO:27:

GGCGTAGGAT GACCCAGCGA T            21

(2) INFORMATION FOR SEQ ID NO:28:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:28:

TCCNNNGCC                                                              9

(2) INFORMATION FOR SEQ ID NO:29:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

GGCNNNACT                                                              9

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

TTGNNNNNNT GT                                                         12

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:31:

TTCNNNNNNA CC                                                         12

(2) INFORMATION FOR SEQ ID NO:32:

(i) SEQUENCE CHARACTERISTICS:
        (A) LENGTH: 2632 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 696...2291
    (D) OTHER INFORMATION:

(xi) SEQUENCE DESCRIPTION: SEQ ID NO:32:

```
ATCGATTTCC GTATATGATG ATACATATGT TAGGTCTCTT ATGGTAGTTT TTAGGGTCTG      60

TCCTGTTTTT TGAAGGCATT GGTTAGGGTC TAGTAAGTAA CTCGTATAAA GAGATGTACT     120

TTTATACGGT ATGTGTGGCG GTTATTTCCA GTGTTTTTTT TCCCTTATTT TGTGGGTTCA     180

TGGAAATAGT ACATATTGAC CTTCTGCACA AGAAGCCATA TTGACAGAGC AGTATGTGAG     240

GACCTTTCTT CTACACAATG TAACAGTCAA TGGTTGTAGT CAATACCACG ACCTTTACGT     300

GCAGTTTTAG AGCGAAACTT CGGTTTTTTG AGACTTACCT CGTGTTTGTG TCTCCCTGGG     360

AATGGAGCCG CGCCACCCTT GTCTATTATG TATAGTCTTA TTTAATCATA GCGATGTTGG     420

TCATCCAGTA CACTTCGGTA GCAACCTTCG TTTGTGATTG TCTTGGTAAT TGCTTCCAAC     480

AACTTTATCC ATCATTGAGA CAGGGGCCAT ATCACCCGCG GGGTCTCAAA GAAGGGGCCC     540

ACTAATAAAA GCACGAGATA AGAATGCCAG CAAAAAAGCT CCGAAATAAT TCTTTTCGTC     600

TTCCCTCCTA GTCTTAACAA GACAAGAGAG AGAGAGAGAA AGAATACTCA CTAGAGATTG     660

TTTCTTTTCT ACTCAACTTA AAGTATACAT ACGCT ATG AAA GCA TTC ACC AGT        713
                                       Met Lys Ala Phe Thr Ser
                                         1               5

TTA CTA TGT GGA CTA GGC CTG TCC ACT ACA CTC GCT AAG GCC ATC TCA       761
Leu Leu Cys Gly Leu Gly Leu Ser Thr Thr Leu Ala Lys Ala Ile Ser
         10                  15                  20

TTG CAA AGA CCG TTG GGT CTA GAT AAG GAC GTT TTG CTG CAA GCT GCG       809
Leu Gln Arg Pro Leu Gly Leu Asp Lys Asp Val Leu Leu Gln Ala Ala
     25                  30                  35

GAA AAA TTT GGT TTG GAC CTC GAC CTG GAT CAT CTC TTG AAG GAG TTG       857
Glu Lys Phe Gly Leu Asp Leu Asp Leu Asp His Leu Leu Lys Glu Leu
 40                  45                  50

GAC TCC AAT GTA TTG GAC GCT TGG GCC CAA ATA GAG CAT TTG TAC CCA       905
Asp Ser Asn Val Leu Asp Ala Trp Ala Gln Ile Glu His Leu Tyr Pro
 55                  60                  65                  70

AAC CAG GTT ATG AGC CTT GAA ACT TCC ACT AAG CCA AAA TTC CCT GAA       953
Asn Gln Val Met Ser Leu Glu Thr Ser Thr Lys Pro Lys Phe Pro Glu
             75                  80                  85

GCA ATC AAA ACG AAG AAA GAC TGG GAC TTT GTG GTC AAG AAT GAC GCA      1001
Ala Ile Lys Thr Lys Lys Asp Trp Asp Phe Val Val Lys Asn Asp Ala
         90                  95                 100

ATT GAA AAC TAT CAG CTT CGT GTC AAC AAG ATT AAG GAC CCT AAA ATC      1049
Ile Glu Asn Tyr Gln Leu Arg Val Asn Lys Ile Lys Asp Pro Lys Ile
     105                 110                 115

CTG GGC ATT GAC CCA AAT GTC ACA CAG TAC ACG GGT TAC TTG GAT GTG      1097
Leu Gly Ile Asp Pro Asn Val Thr Gln Tyr Thr Gly Tyr Leu Asp Val
 120                 125                 130

GAA GAC GAG GAC AAG CAT TTC TTC TTT TGG ACT TTT GAA AGT AGA AAC      1145
Glu Asp Glu Asp Lys His Phe Phe Phe Trp Thr Phe Glu Ser Arg Asn
 135                 140                 145                 150
```

| | |
|---|---|
| GAT CCT GCA AAG GAT CCG GTC ATC CTT TGG TTG AAC GGG GGT CCA GGT<br>Asp Pro Ala Lys Asp Pro Val Ile Leu Trp Leu Asn Gly Gly Pro Gly<br>155 160 165 | 1193 |
| TGT TCT TCA CTA ACC GGG CTG TTC TTT GAA TTA GGA CCC TCA TCC ATT<br>Cys Ser Ser Leu Thr Gly Leu Phe Phe Glu Leu Gly Pro Ser Ser Ile<br>170 175 180 | 1241 |
| GGA CCT GAT TTG AAA CCC ATC GGG AAC CCT TAC TCT TGG AAC AGC AAT<br>Gly Pro Asp Leu Lys Pro Ile Gly Asn Pro Tyr Ser Trp Asn Ser Asn<br>185 190 195 | 1289 |
| GCC ACC GTG ATC TTC CTT GAC CAG CCT GTC AAC GTT GGG TTC TCG TAT<br>Ala Thr Val Ile Phe Leu Asp Gln Pro Val Asn Val Gly Phe Ser Tyr<br>200 205 210 | 1337 |
| TCC GGG TCC TCA GGT GTT TCC AAC ACT GTC GCC GCT GGT AAG GAT GTC<br>Ser Gly Ser Ser Gly Val Ser Asn Thr Val Ala Ala Gly Lys Asp Val<br>215 220 225 230 | 1385 |
| TAT AAC TTC TTG GAG TTG TTC TTC GAT CAG TTC CCT GAA TAC GTC AAC<br>Tyr Asn Phe Leu Glu Leu Phe Phe Asp Gln Phe Pro Glu Tyr Val Asn<br>235 240 245 | 1433 |
| AAG GGC CAA GAT TTC CAC ATC GCT GGG GAA TCC TAC GCC GGC CAT TAC<br>Lys Gly Gln Asp Phe His Ile Ala Gly Glu Ser Tyr Ala Gly His Tyr<br>250 255 260 | 1481 |
| ATC CCT GTT TTT GCC TCT GAA ATT TTG TCT CAC AAG GAC AGA AAC TTC<br>Ile Pro Val Phe Ala Ser Glu Ile Leu Ser His Lys Asp Arg Asn Phe<br>265 270 275 | 1529 |
| AAC TTA ACC TCC GTC TTG ATC GGA AAT GGC CTC ACT GAC CCA TTG ACT<br>Asn Leu Thr Ser Val Leu Ile Gly Asn Gly Leu Thr Asp Pro Leu Thr<br>280 285 290 | 1577 |
| CAG TAT AAC TAT TAC GAA CCA ATG GCC TGT GGT GAA GGT GGC GAA CCA<br>Gln Tyr Asn Tyr Tyr Glu Pro Met Ala Cys Gly Glu Gly Gly Glu Pro<br>295 300 305 310 | 1625 |
| TCT GTT TTG CCC TCG GAG GAA TGC TCT GCT ATG GAA GAC TCT TTG GAA<br>Ser Val Leu Pro Ser Glu Glu Cys Ser Ala Met Glu Asp Ser Leu Glu<br>315 320 325 | 1673 |
| CGT TGT TTG GGC TTG ATC GAG TCG TCG TAT GAC TCG CAA TCG GTC TGG<br>Arg Cys Leu Gly Leu Ile Glu Ser Ser Tyr Asp Ser Gln Ser Val Trp<br>330 335 340 | 1721 |
| TCC TGT GTT CCA GCT ACC ATT TAT TGT AAT AAC GCC CAA TTG GCT CCT<br>Ser Cys Val Pro Ala Thr Ile Tyr Cys Asn Asn Ala Gln Leu Ala Pro<br>345 350 355 | 1769 |
| TAC CAA CGT ACC GGC AGA AAC GTT TAC GAT ATC AGG AAG GAT TGT GAA<br>Tyr Gln Arg Thr Gly Arg Asn Val Tyr Asp Ile Arg Lys Asp Cys Glu<br>360 365 370 | 1817 |
| GGT GGC AAT TTG TGC TAC CCA ACG TTA CAA GAT ATC GAC GAC TAC TTA<br>Gly Gly Asn Leu Cys Tyr Pro Thr Leu Gln Asp Ile Asp Asp Tyr Leu<br>375 380 385 390 | 1865 |
| AAC CAG GAC TAC GTC AAA GAA GCT GTC GGT GCG GAG GTT GAC CAC TAC<br>Asn Gln Asp Tyr Val Lys Glu Ala Val Gly Ala Glu Val Asp His Tyr<br>395 400 405 | 1913 |
| GAA TCC TGT AAC TTC GAT ATC AAC AGA AAT TTC CTG TTT GCG GGT GAT<br>Glu Ser Cys Asn Phe Asp Ile Asn Arg Asn Phe Leu Phe Ala Gly Asp<br>410 415 420 | 1961 |
| TGG ATG AAG CCT TAC CAC ACC GCC GTA ACA GAT CTT TTG AAT CAA GAC<br>Trp Met Lys Pro Tyr His Thr Ala Val Thr Asp Leu Leu Asn Gln Asp<br>425 430 435 | 2009 |
| CTA CCC ATT CTG GTA TAT GCA GGC GAT AAA GAT TTC ATC TGT AAC TGG<br>Leu Pro Ile Leu Val Tyr Ala Gly Asp Lys Asp Phe Ile Cys Asn Trp<br>440 445 450 | 2057 |
| TTG GGT AAT AAG GCG TGG ACG GAT GTC TTG CCA TGG AAG TAC GAC GAA<br>Leu Gly Asn Lys Ala Trp Thr Asp Val Leu Pro Trp Lys Tyr Asp Glu<br>455 460 465 470 | 2105 |

```
GAA TTT GCA AGC CAA AAA GTA CGT AAC TGG ACT GCT TCT ATC ACC GAC    2153
Glu Phe Ala Ser Gln Lys Val Arg Asn Trp Thr Ala Ser Ile Thr Asp
            475                 480                 485

GAG GTC GCT GGT GAA GTC AAA TCC TAC AAG CAC TTC ACC TAT TTG AGA    2201
Glu Val Ala Gly Glu Val Lys Ser Tyr Lys His Phe Thr Tyr Leu Arg
            490                 495                 500

GTC TTC AAT GGT GGC CAC ATG GTT CCA TTT GAC GTC CCT GAA AAC GCC    2249
Val Phe Asn Gly Gly His Met Val Pro Phe Asp Val Pro Glu Asn Ala
            505                 510                 515

TTA AGT ATG GTT AAC GAA TGG ATC CAC GGT GGT TTC TCC TTA TAAAGCGTGT 2301
Leu Ser Met Val Asn Glu Trp Ile His Gly Gly Phe Ser Leu
            520                 525                 530

ATGTGTAGGC ATACCGTTTT TATTATCAGC TACGATCGAA ATATATACGT TTTTATCTAT   2361

GTTACGTTAT ATATTGTAGT CTTAACCATT TGTAAGTTTT GCTTCTTTTC TTTTATTCAT   2421

TTCATAACAT CATACTGTTT TACGTAATAC CATCCTTAAC TTTTTCCACC GAAGGGGAGG   2481

AAGAACTAAA TTCTAGAAAA ATGAAACCAT TAAAAAAAAA GAAAACAATA GAGCTGCTTC   2541

TACAATTTTG CACATCAAAA AAGACCTCCA ACTACCGAGT TTGTAAGTAC AATGTCTCAA   2601

CCCACTCCCA TCATAACTAC AAAATCAGCT G                                 2632

(2) INFORMATION FOR SEQ ID NO:33:

(i) SEQUENCE CHARACTERISTICS:
        (A) LENGTH: 532 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:33:

Met Lys Ala Phe Thr Ser Leu Leu Cys Gly Leu Gly Leu Ser Thr Thr
1               5                   10                  15

Leu Ala Lys Ala Ile Ser Leu Gln Arg Pro Leu Gly Leu Asp Lys Asp
            20                  25                  30

Val Leu Leu Gln Ala Ala Glu Lys Phe Gly Leu Asp Leu Asp Leu Asp
            35                  40                  45

His Leu Leu Lys Glu Leu Asp Ser Asn Val Leu Asp Ala Trp Ala Gln
            50                  55                  60

Ile Glu His Leu Tyr Pro Asn Gln Val Met Ser Leu Glu Thr Ser Thr
65                  70                  75                  80

Lys Pro Lys Phe Pro Glu Ala Ile Lys Thr Lys Lys Asp Trp Asp Phe
            85                  90                  95

Val Val Lys Asn Asp Ala Ile Glu Asn Tyr Gln Leu Arg Val Asn Lys
            100                 105                 110

Ile Lys Asp Pro Lys Ile Leu Gly Ile Asp Pro Asn Val Thr Gln Tyr
            115                 120                 125

Thr Gly Tyr Leu Asp Val Glu Asp Glu Asp Lys His Phe Phe Trp
            130                 135                 140

Thr Phe Glu Ser Arg Asn Asp Pro Ala Lys Asp Pro Val Ile Leu Trp
145                 150                 155                 160

Leu Asn Gly Gly Pro Gly Cys Ser Ser Leu Thr Gly Leu Phe Phe Glu
```

```
                    165                 170                 175
Leu Gly Pro Ser Ser Ile Gly Pro Asp Leu Lys Pro Ile Gly Asn Pro
            180                 185                 190

Tyr Ser Trp Asn Ser Asn Ala Thr Val Ile Phe Leu Asp Gln Pro Val
        195                 200                 205

Asn Val Gly Phe Ser Tyr Ser Gly Ser Ser Gly Val Ser Asn Thr Val
    210                 215                 220

Ala Ala Gly Lys Asp Val Tyr Asn Phe Leu Glu Leu Phe Phe Asp Gln
225                 230                 235                 240

Phe Pro Glu Tyr Val Asn Lys Gly Gln Asp Phe His Ile Ala Gly Glu
                245                 250                 255

Ser Tyr Ala Gly His Tyr Ile Pro Val Phe Ala Ser Glu Ile Leu Ser
            260                 265                 270

His Lys Asp Arg Asn Phe Asn Leu Thr Ser Val Leu Ile Gly Asn Gly
        275                 280                 285

Leu Thr Asp Pro Leu Thr Gln Tyr Asn Tyr Tyr Glu Pro Met Ala Cys
    290                 295                 300

Gly Glu Gly Gly Glu Pro Ser Val Leu Pro Ser Glu Glu Cys Ser Ala
305                 310                 315                 320

Met Glu Asp Ser Leu Glu Arg Cys Leu Gly Leu Ile Glu Ser Ser Tyr
                325                 330                 335

Asp Ser Gln Ser Val Trp Ser Cys Val Pro Ala Thr Ile Tyr Cys Asn
            340                 345                 350

Asn Ala Gln Leu Ala Pro Tyr Gln Arg Thr Gly Arg Asn Val Tyr Asp
        355                 360                 365

Ile Arg Lys Asp Cys Glu Gly Gly Asn Leu Cys Tyr Pro Thr Leu Gln
    370                 375                 380

Asp Ile Asp Asp Tyr Leu Asn Gln Asp Tyr Val Lys Glu Ala Val Gly
385                 390                 395                 400

Ala Glu Val Asp His Tyr Glu Ser Cys Asn Phe Asp Ile Asn Arg Asn
                405                 410                 415

Phe Leu Phe Ala Gly Asp Trp Met Lys Pro Tyr His Thr Ala Val Thr
            420                 425                 430

Asp Leu Leu Asn Gln Asp Leu Pro Ile Leu Val Tyr Ala Gly Asp Lys
        435                 440                 445

Asp Phe Ile Cys Asn Trp Leu Gly Asn Lys Ala Trp Thr Asp Val Leu
    450                 455                 460

Pro Trp Lys Tyr Asp Glu Glu Phe Ala Ser Gln Lys Val Arg Asn Trp
465                 470                 475                 480

Thr Ala Ser Ile Thr Asp Glu Val Ala Gly Glu Val Lys Ser Tyr Lys
                485                 490                 495

His Phe Thr Tyr Leu Arg Val Phe Asn Gly Gly His Met Val Pro Phe
            500                 505                 510

Asp Val Pro Glu Asn Ala Leu Ser Met Val Asn Glu Trp Ile His Gly
        515                 520                 525

Gly Phe Ser Leu
530
```